United States Patent
Naoe et al.

(10) Patent No.: US 8,496,927 B2
(45) Date of Patent: Jul. 30, 2013

(54) CD20 NEGATIVELY CONVERTED B-CELL MALIGNANT LYMPHOMA CELL LINE AND UTILIZATION THEREOF

(75) Inventors: Tomoki Naoe, Nagoya (JP); Akihiro Tomita, Nagoya (JP); Junji Hiraga, Nagoya (JP)

(73) Assignee: National University Corporation Nagoya University, Nagoya-Shi (JP)

( * ) Notice: Subject to any disclaimer, the term of this patent is extended or adjusted under 35 U.S.C. 154(b) by 764 days.

(21) Appl. No.: 12/311,281

(22) PCT Filed: Sep. 21, 2007

(86) PCT No.: PCT/JP2007/068370
§ 371 (c)(1),
(2), (4) Date: Sep. 22, 2009

(87) PCT Pub. No.: WO2008/038587
PCT Pub. Date: Apr. 3, 2008

(65) Prior Publication Data
US 2010/0037328 A1    Feb. 11, 2010

(30) Foreign Application Priority Data
Sep. 25, 2006 (JP) ................................ 2006-259355

(51) Int. Cl.
*A01N 63/00* (2006.01)
*A01K 67/00* (2006.01)
*C12Q 1/00* (2006.01)
*A61K 49/00* (2006.01)

(52) U.S. Cl.
USPC ................. 424/93.7; 800/8; 800/9; 800/10; 435/4; 424/9.2

(58) Field of Classification Search
None
See application file for complete search history.

(56) References Cited

PUBLICATIONS

Matsuo et al. Leukemia Res 1998;22:567-79.*
Wojciechowski et al. J Immunol 2005;174:7859-68.*
Drexler et al. Leukemia Res 2000;24:881-911.*
Davis et al. Clin Cancer Res 1999;5:611-5.*
Nomura et al. Ann Hematol 2005;84:474-6.*
Jilani et al. Blood 2003;102:3514-20.*
B.D. Cheson, "Monoclonal antibody therapy for B-cell malignancies," Seminars in Oncology, vol. 33, Sup. 5, Apr. 2006, pp. 2-14 (Abstract only—1 sheet).
K. Imai et al., "Comparing antibody and small-molecule therapies for cancer," Nat Rev Cancer, vol. 6, Sep. 2006, pp. 714-727.
B. Coiffier et al., "CHOP chemotherapy plus rituximab compared with CHOP alone in elderly patients with diffuse large-B-cell lymphoma," N Engl J Med., vol. 346, No. 4, Jan. 24, 2002, pp. 235-242.
M. H. J. van Oers et al., "Rituximab maintenance improves clinical outcome of relapsed/resistant follicular non-Hodgkin's lymphoma, in patients both with and without rituximab during induction: results of a prospective randomized phase 3 intergroup trial," Blood, vol. 108, No. 10, Jul. 27, 2006, pp. 3295-3301 and a cover page.
T. M. Habermann et al., "Rituximab-CHOP versus CHOP alone or with maintenance rituximab in older patients with diffuse large B-cell lymphoma," J Clin Oncol., vol. 24, No. 19, Jul. 1, 2006, pp. 3121-3127.
M. Pfreundschuh et al., "CHOP-like chemotherapy plus rituximab versus CHOP-like chemotherapy alone in young patients with good-prognosis diffuse large-B-cell lymphoma: a randomised controlled trial by the MabThera International Trial (MInT) Group," Lancet Oncol.vol. 7, May 2006, pp. 379-391.
W. Hiddemann et al., "Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade-Lymphoma Study Group," Blood, vol. 106, No. 12, Dec. 1, 2005, pp. 3725-3732 and a cover page.
M.S. Czuczman, "Prolonged clinical and molecular remission in patients with low-grade or follicular non-Hodgkin's lymphoma treated with rituximab plus CHOP chemotherapy: 9-year follow-up," J Clin Oncol., vol. 22, No. 23, Dec. 1, 2004, pp. 4711-4716.
T. Alvaro-Naranjo et al., "CD20-negative DLBCL transformation after rituximab treatment in follicular lymphoma: a new case report and review of the literature," Ann Hematol., vol. 82, Sep. 2003, pp. 585-588.
Y. Terui et al., "Indentification of CD20 Mutations in Malignant Lymphoma: Can They be Predictors of Response to Rituximab?" Paper presented at: 47th American Society of Hematology Annual Meeting; 106(11), Dec. 12, 2005 (Abstract only—1 sheet).
T. A. Davis et al., "Therapy of B-cell lymphoma with anti-CD20 antibodies can result in the loss of CD20 antigen expression," Clin Cancer Res., vol. 5, Mar. 1999, pp. 611-615.

(Continued)

*Primary Examiner* — Janice Li
(74) *Attorney, Agent, or Firm* — Edwards Wildman Palmer LLP; James E. Armstrong, IV; Kellie K. DiNapoli

(57) ABSTRACT

It is intended to provide a tool, a procedure and so on which are useful in developing a therapeutic strategy efficacious in inhibiting or overcoming the resistance against a CD20-directed molecular-targeted drug. Thus, a CD20-negatively converted B-cell malignant lymphocyte cell line is provided. Also, a model animal indicating the pathological conditions of CD20-negatively converted B-cell malignant lymphocyte is provided. Further, a method of screening a substance, which is efficacious against CD20-positive B-cell malignant lymphocyte or CD20-negatively converted B cell malignant lymphocyte, is provided. Furthermore, a drug against CD20-positive B-cell malignant lymphocyte or CD20-negatively converted B-cell malignant lymphocyte, which is characterized by being used together with a CD20-directed molecular-targeted drug, is provided. In one embodiment, a DNA methylase inhibitor or a histone deacetylase inhibitor is employed as the active ingredient.

7 Claims, 13 Drawing Sheets

PUBLICATIONS

T. Kinoshita et al., "CD20-negative relapse in B-cell lymphoma after treatment with Rituximab," J Clin Oncol. vol. 16, No. 12, Dec. 1998, pp. 3916-3919.

M. Crescenzi et al., "Thermostable DNA polymerase chain amplification of t(14;18) chromosome breakpoints and detection of minimal residual disease," Proc Natl Acad Sci USA. vol. 85, Jul. 1998, pp. 4869-4873.

J. G. Gribben et al., "All advanced stage non-Hodgkin's lymphomas with a polymerase chain reaction amplificable breakpoint of bcl-2 have residual cells containing the bcl-2 rearrangement at evaluation and after treatment," Blood, vol. 78, No. 12, Dec. 15, 1991, pp. 3275-3280 and a cover page.

D. G. Maloney et al., "IDEC-C2B8 (Rituximab) anti-CD20 monoclonal antibody therapy in patients with relapsed low-grade non-Hodgkin's lymphoma," Blood, vol. 90, No. 6, Sep. 15, 1997, pp. 2188-2195 and a cover page.

D.G. Maloney et al., "IDEC-C2B8: results of a phase I multiple-dose trial in patients with relapsed non-Hodgkin's lymphoma," J Clin Oncol., vol. 15, No. 10, Oct. 1997, p. 3266 (Abstract—1 sheet).

G. Egger et al., "Epigenetics in human disease and prospects for epigenetic therapy," Nature, vol. 429, May 27, 2004, pp. 457-463.

M. Binder et al., "The epitope recognized by rituximab," Blood, vol. 108, No. 6, May 16, 2006, pp. 1975-1978 and a cover page.

H. Kiyoi et al., "Immunoglobulin variable region structure and B-cell malignancies," Int J Hematol., vol. 73, Jan. 2001, pp. 47-53.

J. Hiraga et al., "Mechanisms of CD20 negative transformation in Rituximab resistant B cell lymphoma cells", Rinsho Ketsueki, vol. 46, No. 8, 2005, p. 893.

A. Tomita et al., "Re-expression of CD20 surface protein on CD20 negative B cell lymphoma cells", The Japanese Cancer, Association Sokai Kiji, vol. 65, Aug. 28, 2006, pp. 415-416.

A. Ushmorov et al., "Epigenetic processes play a major role in B-cell-specific gene silencing in classicla Hodgkin lymphoma," Blood, vol. 107, No. 6, Mar. 15, 2006, pp. 2493-2500.

I. Matsumura et al., "Zoketuki Shuyo ni Taisuru Bunshi Hyoteki Ryoho", The Journal of the Japanese Society of Internal Medicine, vol. 95, No. 7, Jul. 10, 2006, pp. 147-153.

J. Hiraga et al., "Re-expression of CD20 surface protein on CD20 negative B cell lymphoma cells", Rinsho Ketsueki, vol. 47, Sep. 30, 2006, p. 1053.

A. Tomita et al., "Epigenetic regulation of CD20 protein expression in a novel B-cell lymphoma cell line, RRBL1, established from a patient treated repeatedly with rituximab-containing chemotherapy," Int. J. Hematol., vol. 86, Jul. 15, 2007, pp. 49-57.

A. Tomita et al., "CD20 Insei B Lymph-shu Saibo ni okeru CD20 Kogen Saihatsugen Yudo ni yoru Rituximab Taiseika kokufuku no Kanosei," Hematology & Oncology, vol. 54, No. 5, May 28, 2007, pp. 533-539.

International Search Report dated Oct. 23, 2007, issued on PCT/JP2007/068370.

* cited by examiner

Fig. 2
A Patient
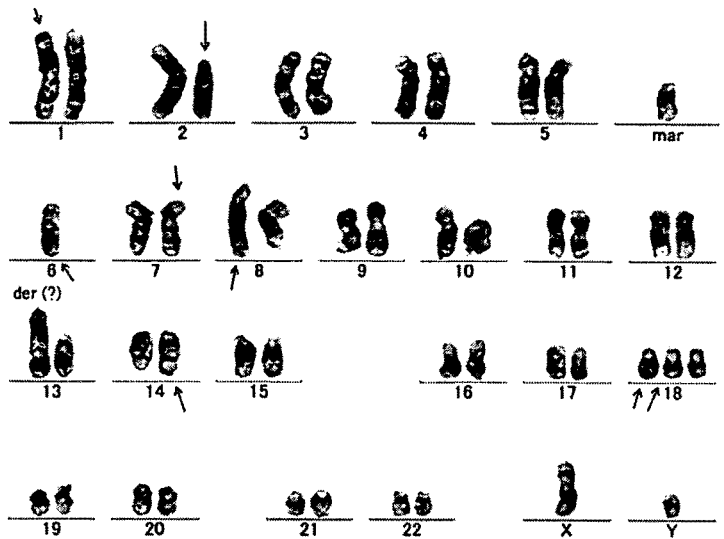
B RRBL1
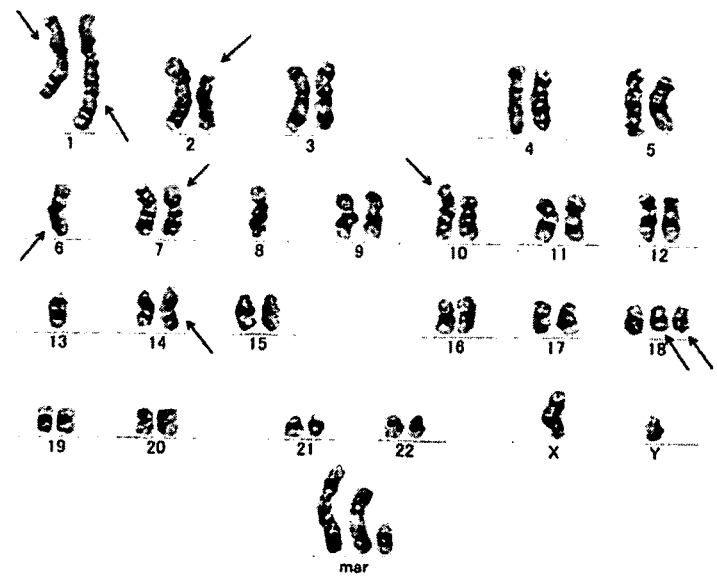

Fig. 3
C
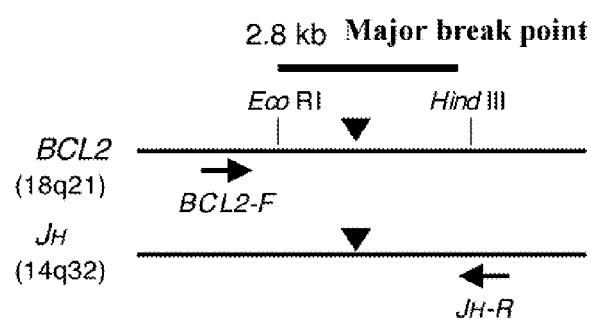
D
E
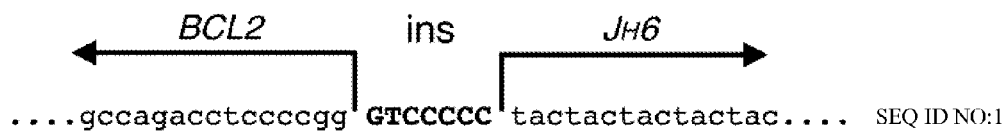
SEQ ID NO:1

Fig. 7
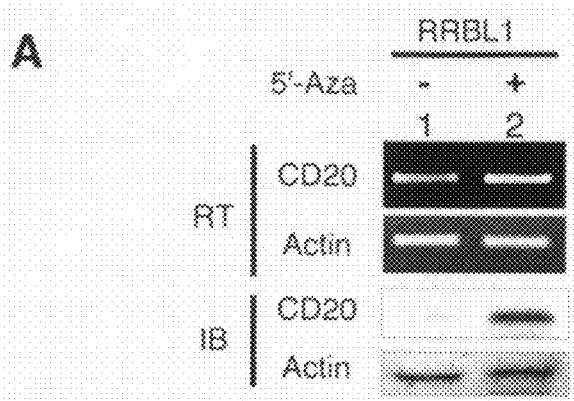
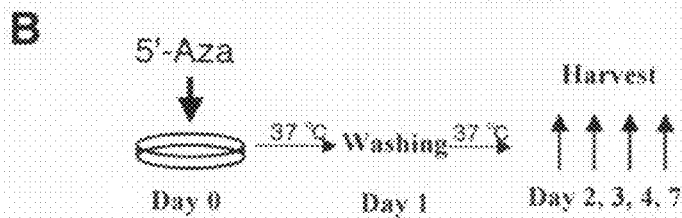
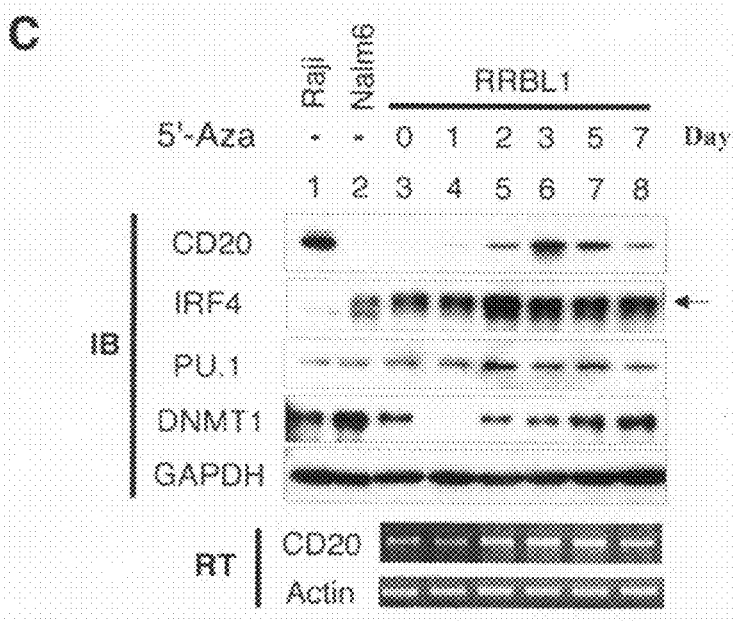

Fig. 8
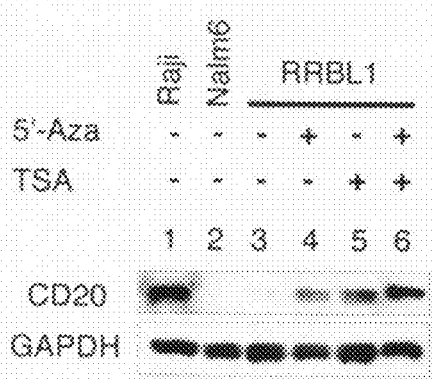
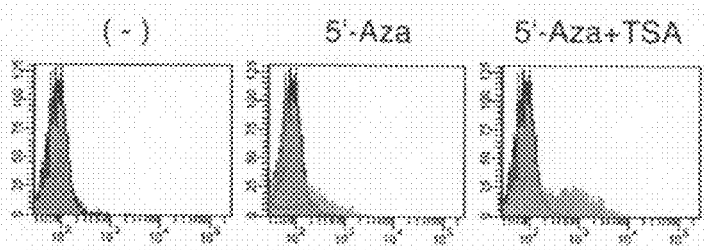
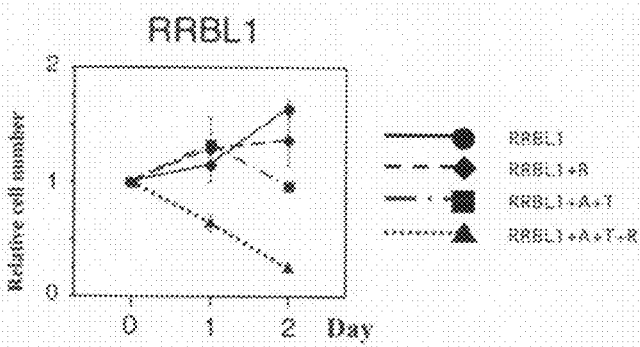

| Surface antigen | Primary Lymphoma Cells | | | RRBL1 Cell Line (Oct. 2005) |
|---|---|---|---|---|
| | Lymph Node (Sep. 1993) | Bone Marrow (Jun. 2004) | Peripheral Blood (Sep. 2004) | |
| B-cell markers | | | | |
| CD10 | 55.1 | 88.3 | 100.0 | 98.0 |
| CD19 | 49.3 | 51.2 | 82.2 | 97.7 |
| CD20 | 58.7 | 0.1 | 4.1 | 3.3 |
| CD23 | | | | 1.8 |
| κ - chain | | 82.8 | 90.1 | 0.7 |
| λ - chain | | 0.1 | 1.8 | 1.2 |
| T/NK cell markers | | | | |
| CD2 | 18.0 | 12.4 | 3.8 | 0.7 |
| CD3 | 17.9 | 12.1 | 1.7 | 1.3 |
| CD4 | 12.3 | | | 1.5 |
| CD5 | 18.1 | 14.8 | 3.0 | 2.2 |
| CD7 | 15.6 | 12.6 | 5.2 | 2.6 |
| CD8 | 5.3 | | | 13.9 |
| CD56 | | | | 2.1 |
| Other markers | | | | |
| CD11c | | | | 2.4 |
| CD16 | | | | 1.5 |
| CD25 | 3.7 | | | 40.4 |
| CD30 | | | | 2.3 |
| CD34 | 0.4 | | | 1.2 |

Fig. 13

| | Number of patients | Clinical stage in rituximab use | | Reactivity | | Rebiopsy of tumor tissues | Rebiopsy of tumor tissues |
|---|---|---|---|---|---|---|---|
| | | At first occurred | At recurred and relapsed | Recurrence and relapse | | | |
| Diffuse large B-cell lymphoma | 51 | 45 | 6 | 13 | | 6 | 3 |
| Follicular lymphoma | 43 | 26 | 17 | 13 | | 7 | 2 |
| Marginal zone B-cell/MALT lymphoma | 8 | 6 | 2 | 2 | | 2 | 0 |
| Burkitt/Burkitt-like lymphoma | 5 | 5 | 0 | 4 | | 2 | 0 |
| Mediastinal large B-cell lymphoma | 4 | 2 | 2 | 1 | | 0 | 0 |
| Intravascular large B cell lymphoma | 4 | 4 | 0 | 2 | | 1 | 0 |
| Mantle cell lymphoma | 4 | 3 | 1 | 1 | | 1 | 0 |
| Lymphoplasmacytic lymphoma | 3 | 3 | 0 | 0 | | 0 | 0 |
| Chronic lymphoid leukemia | 2 | 1 | 1 | 0 | | 0 | 0 |
| Total (number of patients) | 124 | 96 | 28 | 36 | | 19 | 5 |
| | | | | (36/124; 29.0%) | | (19/36; 52.5%) | (5/19; 26.3%) |

CD20 NEGATIVELY CONVERTED B-CELL MALIGNANT LYMPHOMA CELL LINE AND UTILIZATION THEREOF

SEQUENCE LISTING

The instant application contains a Sequence Listing which has been submitted in ASCII format via EFS-Web and is hereby incorporated by reference in its entirety. Said ASCII copy, created on Sep. 5, 2012, is named 83779305.txt and is 789 bytes in size.

TECHNICAL FIELD

The present invention relates to a technology useful for developing a treatment or a method for treating B-cell malignant lymphoma. The technologies disclosed in the present specification are particularly useful for developing a treatment or a method for treating pathological conditions led to indication of resistance to a CD20-directed molecular targeting drug by negative conversion of CD20 among B-cell malignant lymphomas (CD20 negatively converted B-cell malignant lymphoma).

BACKGROUND ART

Rituximab is a chimeric monoclonal antibody that specifically recognizes a CD20 antigen specifically expressed in B-cell lymphocytes (Non-patent Documents 1 and 2). A CD20 antigen is widely expressed on B-cell malignant tumors, typically including such as follicular malignant lymphoma that develops relatively slow and diffuse malignant lymphoma that develops aggressively. Rituximab has been administered as a molecular targeting drug against a CD20 antigen in addition to chemotherapy for these B-cell malignancies expressing the CD20 antigen (Non-patent document 3 to 8). Although the CHOP chemotherapy has been utilized for B-cell lymphoma patients for more than 25 years, unfortunately, the cure rate of diseases has not been improved, even with a combination with other chemotherapies or change of a dosage. However, in recent reports, it has been confirmed that the cure and disease-free survival rates of the diseases are improved significantly by using rituximab for CD20 positive B-cell malignant lymphoma in combination with conventional chemotherapies based on CHOP (Non-patent Documents 3 to 8).

Although 5 years have passed since rituximab was started to be clinically used, the cure rate for CD20 positive malignant lymphomas is still unsatisfactory, and the considerable number of patients treated with rituximab have undergone the progression and transformation of a tumor that is unreative to rituximab (Non-patent Document 9 to 12). Recently, Terui et al reported that 5 out of 48 CD20 positive lymphoma patients showed rituximab resistance and genetic mutations in the CD20-coding sequence region in 10 out of 48 patients were confirmed (Non-patent document 10). A conformational change in the CD20 protein caused by genetic mutations has been speculated to contribute to one of mechanisms of rituximab resistance. However, the relationship between genetic mutations in the CD20-coding sequence region and rituximab resistance is not clearly indicated, which also suggested existence of mechanisms of rituximab resistance other than genetic mutations.

Recently, we had a patient of CD20 positive malignant B-cell lymphoma (diagnosis in onset) transformed to a tumor having a feature of rituximab resistance after repeated administration of rituximab. Disease progression of this patient worsened during the rituximab administration and CD20 expression in lymphoma cells was not observed in pathological findings and studies by flow cytometry (FCM) at the point.

Non-patent Document 1: Cheson B D. Monoclocal antibody therapy for B-cell malignancies. Semin Oncol. April 2006; 33(2 Suppl 5): S2-14.

Non-patent Document 2: Imai K, Takaoka A. Comparing antibody and small-molecule therapies for dancer. Nat Rev Cancer. September 2006; 6(9): 714-727.

Non-patent Document 3: Coiffier B, Lepage E, Briere J, et al. CHOP chemotherapy plus rituximab compared with CHOP alone in elderly patients with diffuse large-B-cell lymphoma. N Engl J Med. Jan. 24, 2003; 346(4): 235-242.

Non-patent Document 4: van Oers M H, Klasa R, Marcus R E, et al. Rituximab maintenance improves clinical outcome of relapsed/resistant follicular non-Hodgkin's lymphoma, both in patients with and without rituximab during induction: results of a prospective randomized phase III intergroup trial. Blood. Jul. 27, 2006.

Non-patent Document 5: Habermann T M, Weller E A, Morrison V A, et al. Rotuximab-CHOP versus CHOP alone or with maintenance rituximab in order patients with diffuse large B-cell lymphoma. J Clin Oncol. Jul. 1, 2006; 24(19): 3121-3127.

Non-patent Document 6: Pfreundschuh M, Trumper L, Osterborg A, et al. CHOP-like chemotherapy plus rituximab versus CHOP-like chemotherapy alone in young patients with good-prognosis diffuse large-B-cell lymphoma: a randomised controlled trial by the MabThera International Trial (MInT) Group. Lancet Oncol. May 2006; 7(5): 379-391.

Non-patent Document 7: Hiddemann W, Kneba M, Dreyling M, et al. Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group. Blood. Dec. 1, 2005; 106(12): 3725-3732.

Non-patent Document 8: Czuczman M S, Weaver R, Alkuzweny B, Berlfein J, Grillo-Lopez A J. Prolonged clinical and molecular remission in patients with low-grade or follicular non-Hodgkin's lymphoma treated with rituximab plus CHOP chemotherapy: 9-year follow-up. J Clin Oncol. Dec. 1, 2004; 22(23): 4711-4716.

Non-patent Document 9: Alvaro-Naranjo T, Jean-Martinez J, Guma-Padro J, Bosch-Princep R, Salvado-Usach M T. CD20-negative DLBCL transformation after rituximab treatment in follicular lymphoma: a new case report and review of the literature. Ann Hematol. September 2003; 2003; 82(9): 585-588.

Non-patent Document 10: Yasuhito Terui T S, Yuji Mishima, Yuko Mishima, Natsuhiko Sugimura, Kiyotsugu Kojima, Masahiro Yokoyama, Kiyohiko Hatake. Identification of CD20 Mutations in Malignant Lymphoma: Can They Be Predictors of Response to Rituximab? Paper presented at: 47th American Society Of Hematology Annual Meeting; Dec. 12, 2005, 2005; Atlanta.

Non-patent Document 11: Davis T A, Czerwinski D K, Levy R. Therapy of B-cell lymphoma with anti-CD20 antibodies can result in the loss of CD20 antigen expression. Clin Cancer Res. March 1999; 5(3): 611-615.

Non-patent Document 12: Kinoshita T, Nagai H, Murate T, Saito H. CD20-negative relapse in B-cell lymphoma after treatment with Rituximab. J Clin Oncol. December 1998; 16(12): 3916.

Non-patent Document 13: Crescenzi M, Seto M, Herzig G P, Weiss PD, Griffith R C, Korsmeyer S J. Thermostable DNA polymerase chain amplification of t(14;18) chromosome breakpoints and detection of minimal residual disease. Proc Natl Acad Sci USA. July 1988; 85(13): 4869-4873.

Non-patent Document 14: Gribben J G, Freedman A, Woo S D, et al. All advanced stage non-Hodgkin's lymphomas with a polymerase chain reaction amplifiable breakpoint of bcl-2 have residual cells containing the bcl-2 rearrangement at evaluation and after treatment. Blood. Dec. 15, 1991; 78(12): 3275-3280.

Non-patent Document 15: Maloney D G, Grillo-Lopez A J, White C A, et al. IDEC-C2B8(Rituximab) anti-CD20 monoclonal antibody therapy in patients with relapsed low-grade non-Hodgikin's lymphoma. Blood. Sep. 15, 1997; 90(6): 2188-2195.

Non-patent Document 16: Maloney D G, Grillo-Lopez Aj, Bodkin D J, et al. IDEC-C2B8: results of a phase I multiple-dose trial in patients with relapsed non-Hodgkin's lymphoma. J Clin Oncol. October 1997; 15(10): 3266-3274.

Non-patent Document 17: Egger G, Liang G, Aparicio A, Jones P A. Epigenetics in human disease and prospects for epigenetic therapy. Nature. May 27 2004; 429(6990): 457-463.

Non-patent Document 18: Binder M, Otto F, Mertelsmann R, Veelken H, Trepel M. The epitope recognized by rituximab. Blood. May 16, 2006.

Non-patent Document 19: Kiyoi H, Naoe T. Immunoglobulin variable region structure and B-cell malignancies. Int J Hematol. January 2001; 73(1): 47-53.

DISCLOSURE OF THE INVENTION

Problems to be Solved by the Invention

In a case of leading to indication of resistance to rituximab, no effective alternative therapy exists at present, and it has been an urgent request to overcome the resistance to rituximab. If the resistance can be overcome, continuous use of rituximab becomes possible, which will be a good news to a large number of patients. Further, contribution to the medical field is also innumerable. Incidentally, not limited to rituximab, resistance to other CD20-directed molecular targeting drugs is predicted to generate based on the same mechanism although not becoming actually at present. Furthermore, molecular targeting drugs that will be developed in the future are also concerned about occurrence of resistance based on the same mechanism.

Thus, an object of the present invention is to provide a tool, a means and the like useful for developing a therapeutic strategy efficacious in inhibiting or overcoming the resistance to a CD20-directed targeting drug typically including rituximab. Further, an object is also to provide a drug and a therapeutic method utilized in the therapeutic strategy.

Means for Solving the Problems

The present inventors made studies to aim for development of a therapeutic strategy efficacious against CD20 negatively converted B cell malignant lymphoma. As a result, the following findings and outcomes were obtained.

(1) We have succeeded in establishing a cell line from tumor cells of a patient having resistance to rituximab that is a CD20-directed molecular targeting drug (CD20 negatively converted malignant lymphoma cell line) because of CD20 negative conversion.

(2) A mechanism of decrease in CD20 expression was analyzed by using this cell line (RRBL1). As a result, it was strongly suggested that decrease in a CD20 mRNA expression level was one important factor of CD20 negative conversion. Interestingly, sufficient CD20 protein expression was confirmed in a subcell line RRBL2 established by long-term culture of RRBL1. These results indicate that it is possible to reexpress CD20 in CD20 negatively converted cells, and at the same time, suggest that inducing reexpression of CD20 becomes an effective therapeutic strategy against CD20 negatively converted B-cell malignant lymphoma.

Herein, in consideration of high specificity of a molecular targeting drug, the above mechanism leading to acquisition of resistance found by the present inventors could be said to have high universality. Therefore, a strategy of inducing reexpression of CD20 is largely expected to be efficacious against various pathological conditions leading to acquisition of resistance to a molecular targeting drug by CD20 negative conversion, not limited to pathological conditions derived from RRBL1.

(3) As various medicaments were added to RRBL1 and CD20 expression was analyzed with elapse of time, induction of CD20 mRNA and CD20 protein was possible by specific drugs (5-aza-2'-deoxycytidine that is a DNA methylase inhibitor and Trichostatin A that is a histone deacetylase inhibitor). That is, it was revealed that a DNA methylase inhibitor and a histone deacetylase inhibitor are promising as therapeutic drugs against CD20 negatively converted B-cell malignant lymphoma. Further, it was supported that an experiment system using RBBL1 is an effective procedure for finding out a compound useful for a therapeutic strategy based on induction of CD20 expression.

(4) RRBL1 was transplanted to immunodeficient mice to study whether a tumor was formed or not; and as a result, formation and growth of the tumor were observed, and it was revealed that RBBL1 cells can be maintained in vivo environment of the immunodeficient mice. When RBBL1 cells were intravenously administered to observe formation of a tumor, pathological findings extremely similar to a patient having the original RBBL1 cells were shown. Thus, the present inventors successfully prepared an in vivo model reproducing CD20-negatvely converted B-cell malignant lymphoma. It was indicated that RBBL1 was extremely useful for proceeding development of a therapeutic strategy not only in vitro but also in vivo.

The present invention is based on the above findings and outcomes and provides the following cell line, screening method and the like.

[1] A CD20 negatively converted B-cell malignant lymphoma cell line derived from B-cell malignant lymphoma in which CD20 protein expression is negatively converted.

[2] The cell line according to [1], wherein the B-cell malignant lymphoma is diffuse B-cell malignant lymphoma transformed from follicular lymphoma.

[3] The cell line according to [1], wherein negative conversion of CD20 protein expression is caused by decrease in a CD20 mRNA expression level.

[4] The cell line according to [3] having potential ability to express CD20 protein.

[5] The cell line according to [1], which is CD10 positive, CD19 positive, CD20 negative, and immunoglobulin light chain (κ chain and λ chain) negative.

[6] The cell line according to [1], which is a cell line specified by accession No: FERM BP-10910.

[7] A model animal indicating pathological conditions of CD20 negatively converted B-cell malignant lymphoma, which is prepared by transplanting or administering the cell line according to any of [1] to [6] to an immunodeficient non-human animal.

[8] The model animal according to [7], wherein the immunodeficient non-human animal is a NOD/SCID mouse.

[9] A method for screening a substance which is efficacious against CD20 positive B-cell malignant lymphoma or CD20 negatively converted B-cell malignant lymphoma, including the steps of:
(1) culturing CD20 negatively converted B-cell malignant lymphoma cells in the presence of a test substance; and
(2) measuring a CD20 mRNA expression level or a CD20 protein expression level in the cells after culturing to evaluate CD20 expression inducing ability of the test substance.

[10] The method for screening according to [9], further including the following steps of:
(3) culturing CD20 negatively converted B-cell malignant lymphoma cells in the presence of the test substance selected based on a result of the step (2);
(4) culturing the cells after the step (3) in the presence of a CD20-directed molecular targeting drug; and
(5) measuring the number of survival cells to determine efficacy of the test substance.

[11] The method for screening according to [9], further including the following steps of:
(3) culturing CD20 positive B-cell malignant lymphoma cells and CD20 negatively converted B-cell malignant lymphoma cells in the presence of the test substance selected based on a result of the step (2) and a CD20-directed molecular targeting drug; and
(4) measuring the number of survival cells to determine efficacy of the test substance.

[12] The method for screening according to any of [9] to [11], wherein the CD20 negatively converted B-cell malignant lymphoma cell is the cell line according to any of [1] to [6].

[13] A method for screening a substance which is efficacious against CD20 positive B-cell malignant lymphoma or CD20 negatively converted B-cell malignant lymphoma, including the steps of:
(1) culturing the cell line according to any of [1] to [6] in the presence of a test substance;
(2) culturing the cells after the step (1) in the presence of a CD20-directed molecular targeting drug; and
(3) measuring the number of survival cells to determine efficacy of the test substance.

[14] A method for screening a substance which is efficacious against CD20 positive B-cell malignant lymphoma or CD20 negatively converted B-cell malignant lymphoma, including the steps of:
(1) culturing the cell line according to any of [1] to [6] in the presence of a test substance and a CD20-directed molecular targeting drug; and
(2) measuring the number of survival cells to determine efficacy of the test substance.

[15] A method for screening a substance which is efficacious against CD20 negatively converted B-cell malignant lymphoma, including the steps of:
(1) administering a test substance to the model animal according to [7] or [8]; and
(2) examining change of pathological conditions characteristic to CD20 negative B-cell malignant lymphoma indicated in the model animal.

[16] A drug against CD20 positive B-cell malignant lymphoma or CD20 negatively converted B-cell malignant lymphoma, containing a compound for increasing a CD20 protein expression level and being used in combination with a CD20-directed molecular targeting drug.

[17] The drug according to [16], wherein the compound has an action of increasing a CD20 mRNA expression level.

[18] The drug according to [16], wherein a DNA methylase inhibitor and/or a histone deacetylase inhibitor is used as the compound.

[19] A method for treating CD20 positive B-cell malignant lymphoma or CD20 negatively converted B-cell malignant lymphoma, wherein a DNA methylase inhibitor and/or a histone deacetylase inhibitor, and a CD20-directed molecular targeting drug are used in combination.

[20] Use of a DNA methylase inhibitor and/or a histone deacetylase inhibitor for producing a drug against CD20 positive B-cell malignant lymphoma or CD20 negatively converted B-cell malignant lymphoma, wherein drug efficacy is exerted by being used in combination with a CD20-directed molecular targeting drug.

BRIEF DESCRIPTION OF DRAWINGS

FIG. 2 shows chromosomal abnormalities of the RRBL1 cells and the lymphoma cells obtained from the patient having the original RRBL1 cells. FIG. 2(A) is the patient sumple, and FIG. 2(B) is RRBL1 cells. The specific chromosomal abnormalities are as follows. (A) 47, XY, t(1;7)(p36;p15), t(2;8) (p12;q24), −6, add(6)(q21), t(14;18)(q32;q21), +18. der(18) t(14; 18), +der(?)t(?;13)(?;q12), +mar2. (B)47, XY, der(1)t(1; ?7)(p36;p15), dup(1)(q21q42), add(2)(p11), −6, del(6) (q15q21), add(7)(p11), −8, add(10)(p13), −13, t(14;18)(q32; q21), +der(18)t(14;18), +3mar.

FIG. 3 shows chromosomal abnormalities of the RRBL1 cells and the lymphoma cells obtained from the patient having the original RRBL1 cells. FIG. 3(C) illustrates reciprocal translocation of the BCL2 gene and the JH gene detected in t(14;18)(q32;q21). The translocation points were illustrated with black arrows. Specific translocation points in JH are reported from J1 to J6 (Non-patent Documents 13 and 19). PCR primers used for the amplification of the translocation points are indicated by black arrows. In FIG. 3(D), genomic DNA was extracted from RRBL1 cells and cells obtained in each clinical stage from a patient, the source of the RRBL1 cells, and PCR was performed to amplify BCL2-JH translocation point. A single band with the same size was confirmed in all subjects. Ad-LN indicates the lymph node harvested from the patient on admission; TF-PB indicates lymphoma cells from the patient's peripheral blood in July 2004; RRBL1a (after culturing for 90 days); RRBL1b (after culturing for 120 days); and RRBL1 cells cultured in vitro. FIG.

3(E) shows a genomic sequence (SEQ ID NO: 1) of the BCL2-JH6 translocation point (GenBank accession no. DQ979790).

Figure 4:
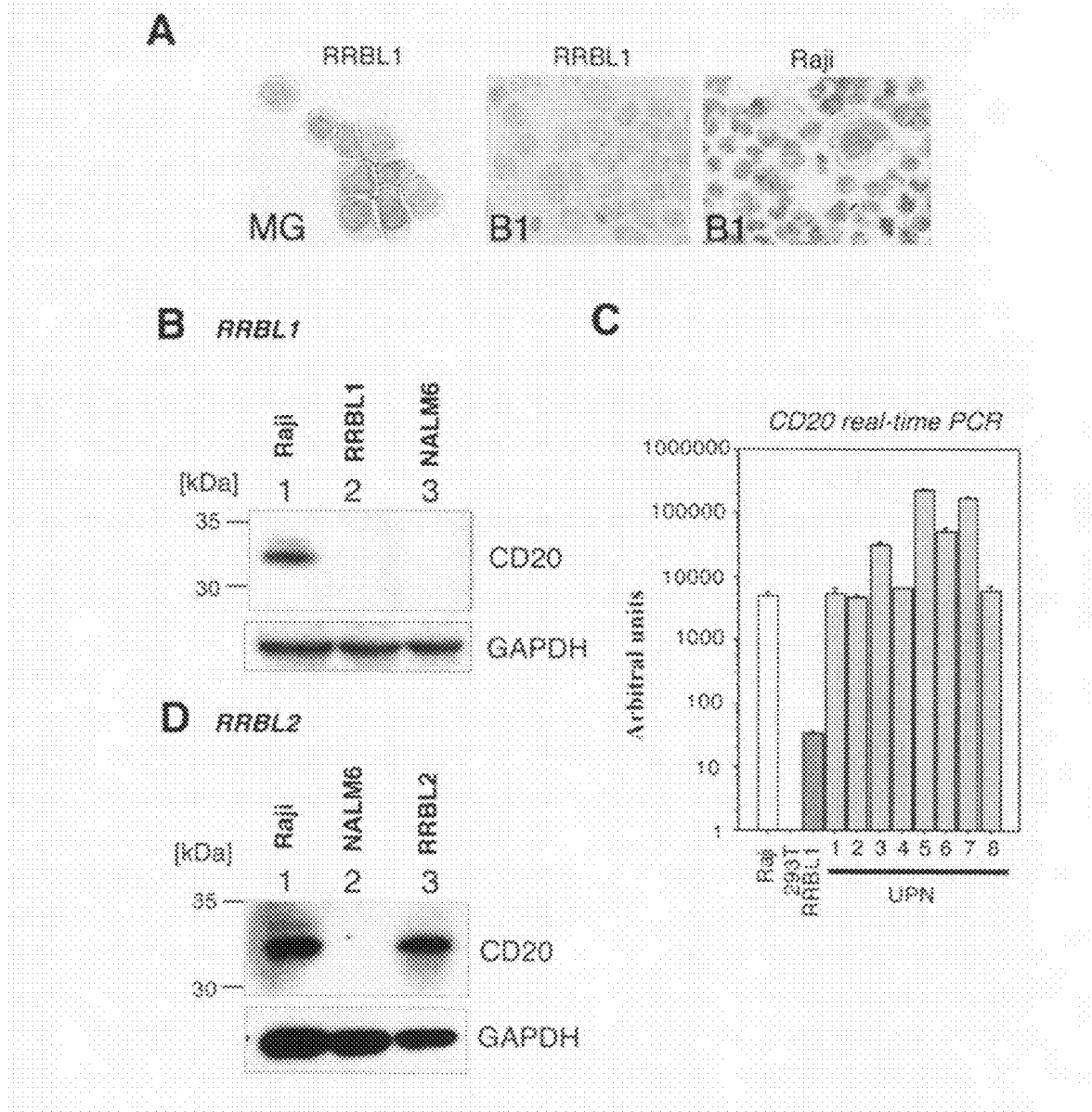

FIG. 4 shows CD20 protein and mRNA expression in RRBL1 cells. (A) Immunostaining with an anti-CD20 antibody (B1 monoclonal antibody) in RRBL1 and Raji cells. RRBL1 cells do not show CD20 expression, but Raji cells express CD20 at the surface. MG inidicates Amy-Giemsa staining. FIG. 4(B) illustrates whole cell lysates obtained from Raji cells, RRBL1 cells and NALM6 cells, and western immunoblotting using a CD20 antibody was preformed. CD20 protein expression was detected in Raji cells (lane 1), but not in RRBL1 cells or NALM6 cells (lanes 2 and 3). Western blotting was performed for GAPDH as a positive control. FIG. 4(C) illustrates quantitative RT-PCR for detecting CD20 mRNA. 293T cells were used as a negative control (lane 2). The level of CD20 mRNA expression of RRBL1 cells (lane 3) was significantly lower than that of the positive control Raji cells (lane 1). Further, RNA was extracted from cells obtained from a CD20 positive B-cell malignant lymphoma patient and the same analysis was performed (lanes 4 to 11). The CD20 mRNA expression level in RRBL1 cells was significantly lower than that of these RNAs. In FIG. 4(D), RRBL1 cells were passage-cultured and a subcell line, RRBL2, was established. The whole cell lysates were extracted from the cells and western blotting using an anti-CD20 antibody was performed. In RRBL2 cells, CD20 expression was confirmed (lane 3).

Figure 5:
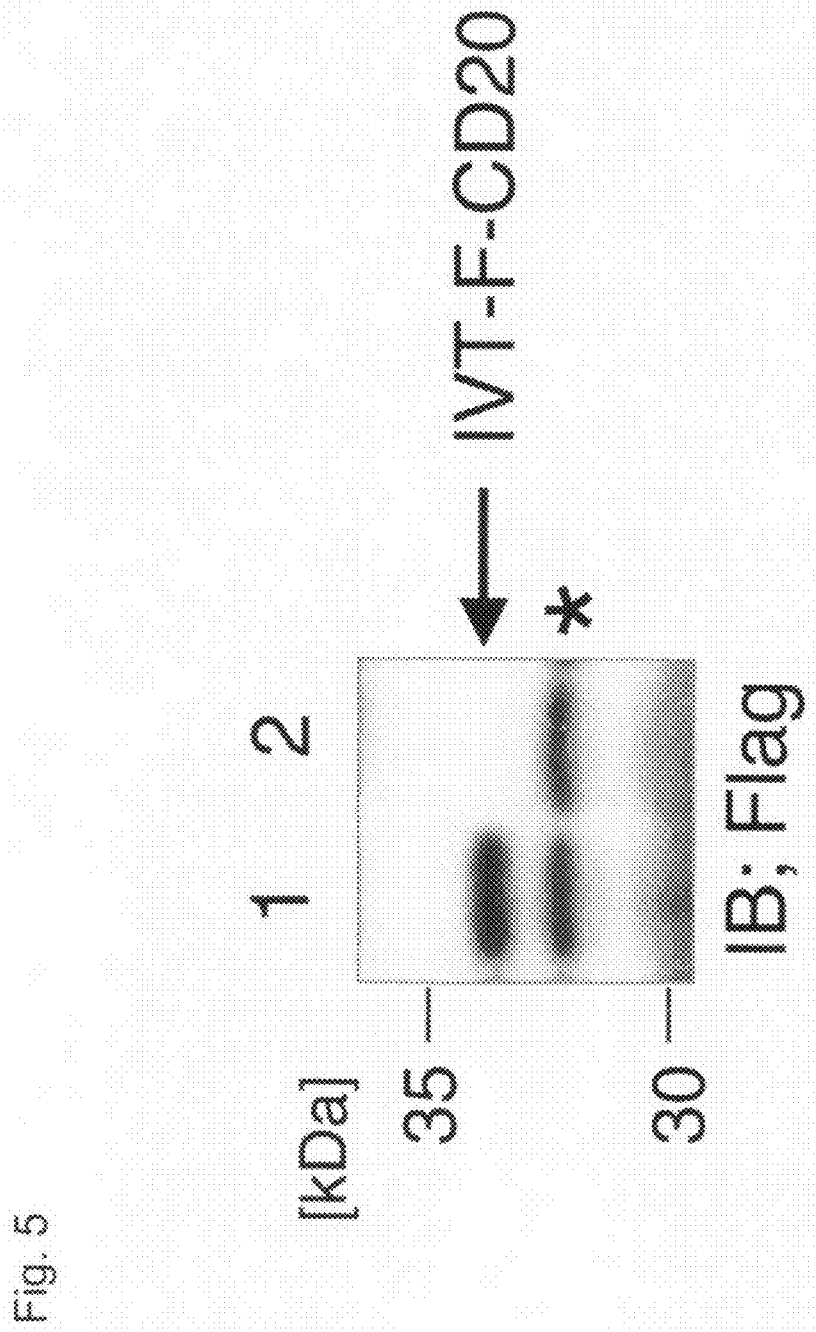

FIG. 5 shows a result of detecting (western blotting) protein expressed by in vitro translation with an anti-Flag antibody. Lane 1 is a translated product from a vector into which CDS of CD20 genes is inserted, and lane 2 is a translated product only from a T7Ts-Flag vector.

Figure 6:
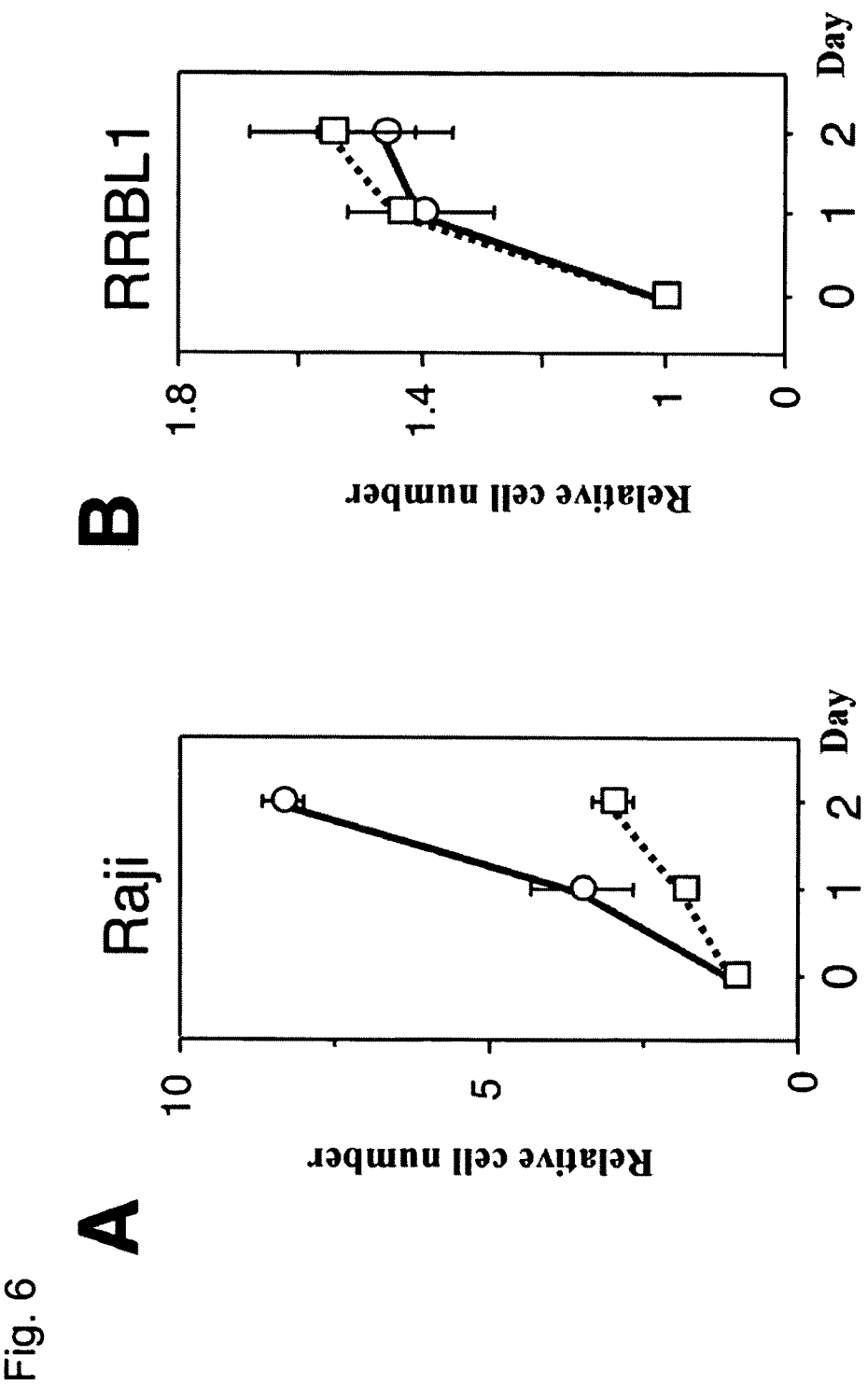

FIG. 6 is a view illustrating resistance of RRBL1 cells against rituximab. The number of Raji cells (A) and RRBL1 cells (B) are indicated respectively by line graphs.

FIG. 7 illustrates reexpression of CD20 mRNA and CD20 protein in RBBL1 cells. FIG. 7(A) shows results of analyzing the RRBL1 cells treated with 5-aza-2'-deoxycytidine by RT-PCR. FIG. 7(B) shows description of the experimental procedure. FIG. 7(C) shows a result of western blotting using RNA and protein extracted from cells after culturing. Raji (lane 1) and NALM6 (lane 2) were respectively used as a positive control and a negative control of CD20 expression.

FIG. 8(A) shows a result of western blotting analysis of RRBL1 cells treated with Aza and TSA. FIG. 8(B) shows a result of analyzing RRBL1 cells cultured in the presence of Aza or in the presence of Aza and TSA by FCM. FIG. 8(C) illustrates comparison of resistance to rituximab. RRBL1 cells (untreated group) and RRBL1 cells treated with Aza and TSA (treated group) were cultured in the absence of rituximab (● and ■) or in the presence of rituximab (♦ and ▲), and then the number of living cells was compared.

Figure 9:
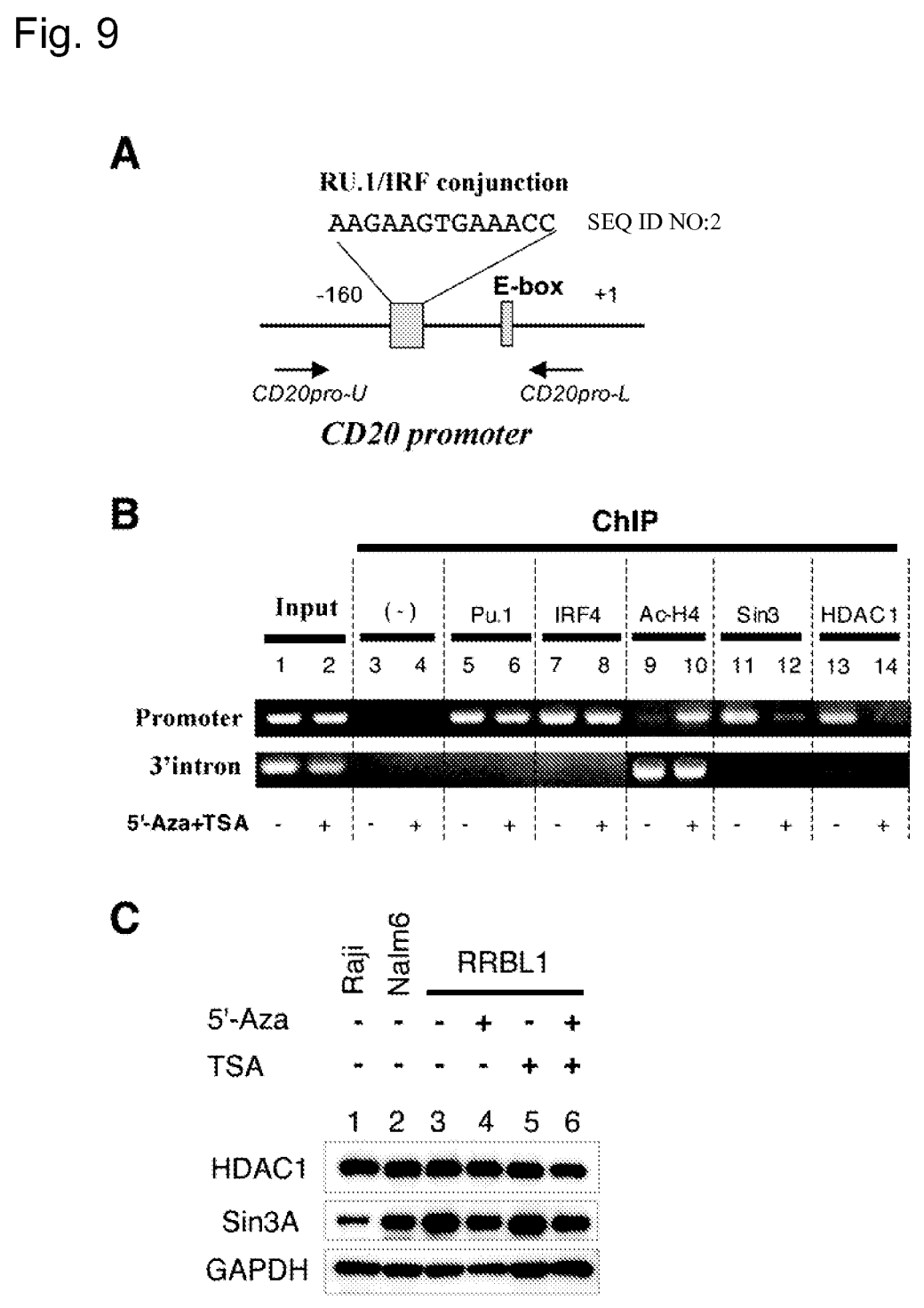

FIG. 9 shows an analysis of CD20 transcriptional regulation in a CD20 gene promoter. FIG. 9(A) illustrates a structure of the CD20 gene promoter (SEQ ID NO: 2). Arrows in the figure (CD20pro-U, CD20pro-L) indicate positions of PCR primers used in the Chromatin immunoprecipitation assay (ChIP). FIG. 9(B) shows results of the ChIP assay using an anti-Pu.1 antibody, anti-IRF4 antibody, anti-acetylation H4 (Ac-H4) antibody, anti-Sin3 antibody and anti-HDAC1 antibody. FIG. 9(C) shows results of western blotting using an anti-CD20 antibody and an anti-GAPDH antibody.

Figure 10:
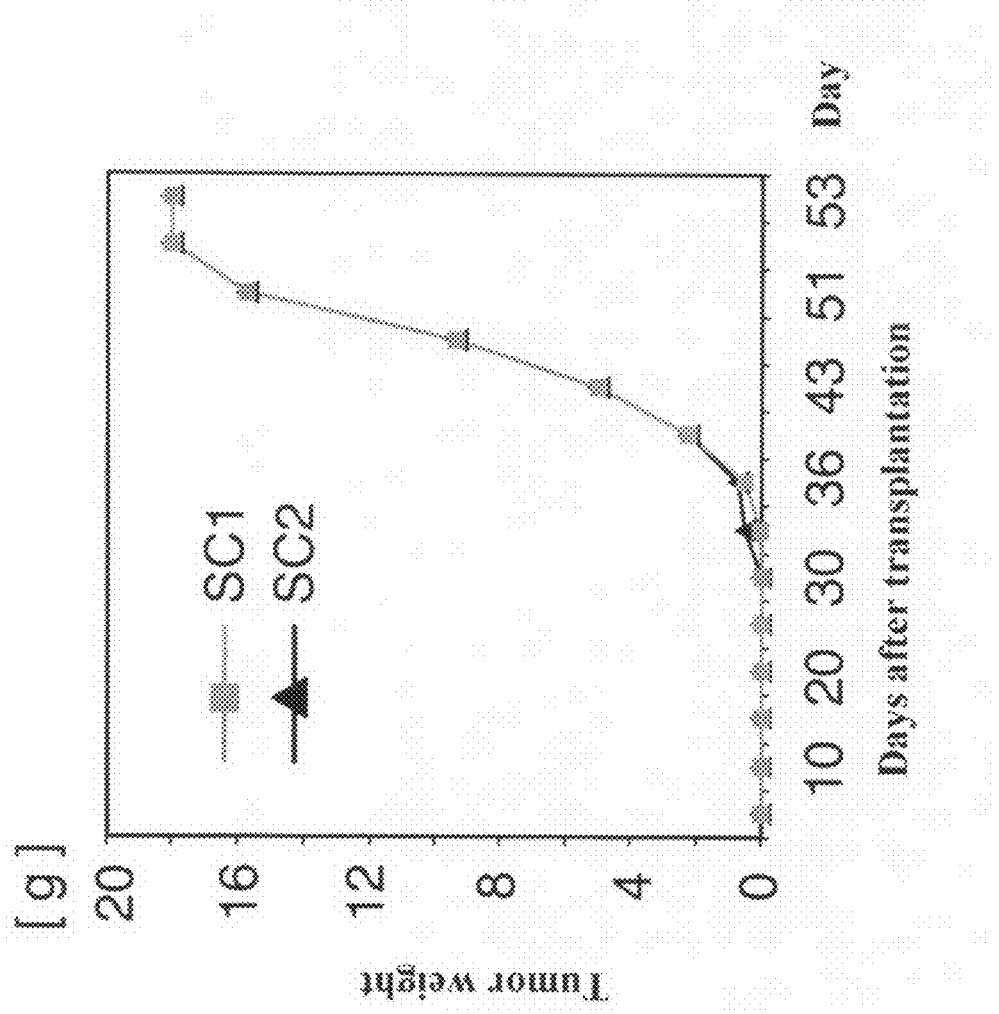

FIG. 10 illustrates a weight of a tumor formed in a NOD/SCID mouse to which RRBL1 cells are transplanted. The RRBL1 cells ($5 \times 10^6$) were subcutaneously injected at the dorsal region of the NOD/SCID immunodeficient mouse. A tumor visually detected was observed on 30 days after the administration, and a size and a weight of the tumor were calculated. The same analysis was performed on two mice (SC1 and SC2) and almost the same courses were observed.

Figure 11:
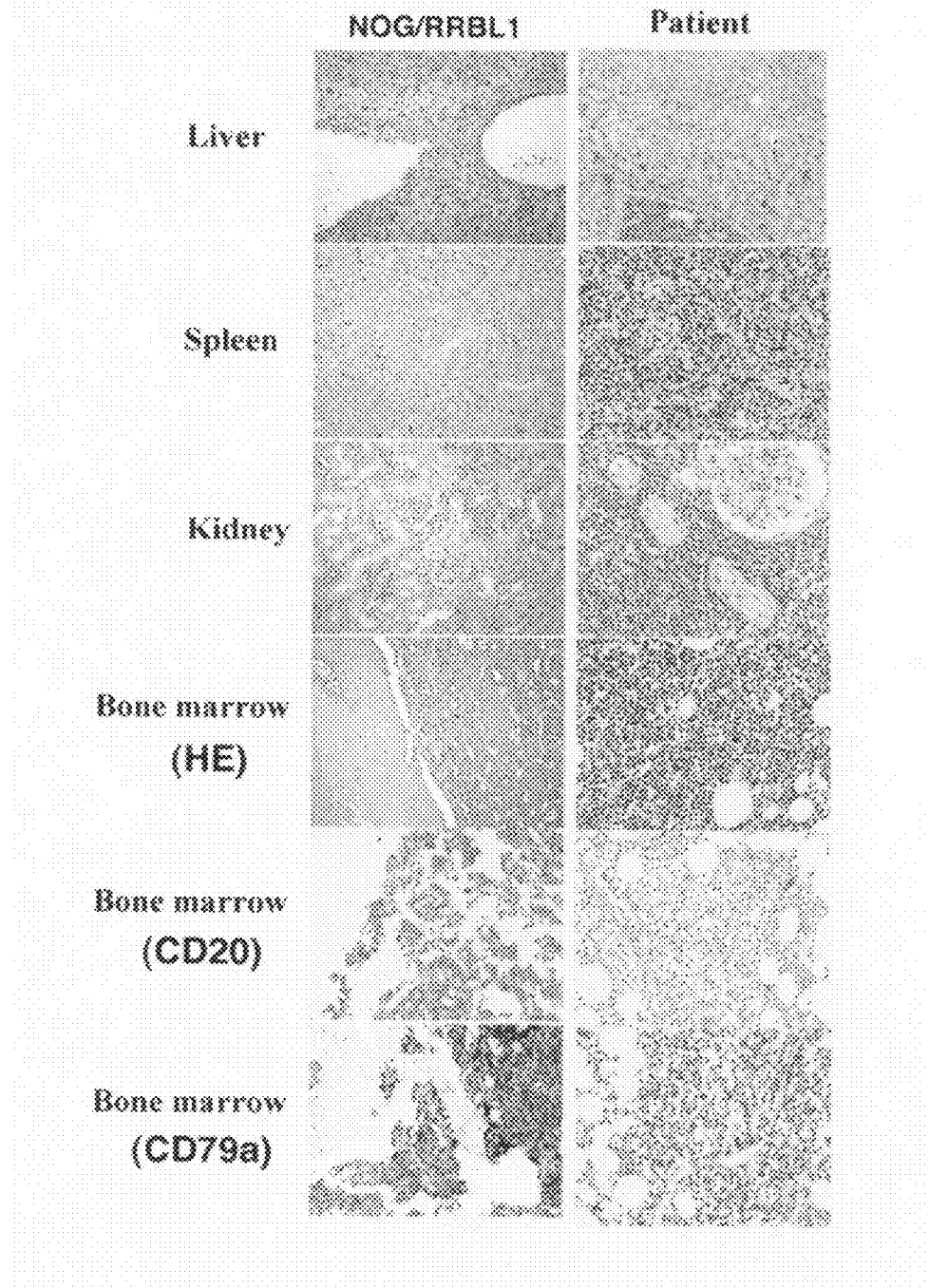

FIG. 11 shows comparison between pathologic tissues of the NOD/SCID mouse administered RRBL1 cells (left figure) and autopsy tissue findings of the patient having the original RRBL1 cells (right figure). The RRBL1 cells ($5 \times 10^6$) were intravenously administered to the NOD/SCID mice. Eight weeks after transplantation, organs were removed from the mice under appropriate anesthesia and subjected to pathological examinations. Diffuse infiltration of RRBL1 cells into organs such as the liver, spleen, kidney and bone marrow (HE stain, left figure) was observed. The tumor cells showed negative in an immunostaining using an anti-CD20 antibody, and the tumor cells showed positive in immunostaining using an anti-CD79a antibody recognizing B-cells. Autopsy tissue findings of the patient having the original cell line were indicated on the right column. The tumor cells were diffusely infiltrated into the liver, spleen, kidney and bone marrow, and showed negative in immunostaining using an anti-CD20 antibody. In the study using an anti-CD79a antibody, the tumor cells showed positive and were confirmed to be B-cell lymphoma cells. From these results, pathological findings of the NOD/SCID mice to which RRBL1 cells were transplanted were confirmed to well reflect pathological conditions of the patient.

FIG. 12 shows surface antigens of primary lymphoma cells and RRBL1 cells.

FIG. 13 shows use experiences of rituximab against CD20 positive B-cell malignant lymphoma and frequency of CD20 negative conversion in the Hospital of Nagoya University, School of Medicine. Cases of CD20 positive malignant lymphoma in which rituximab-containing chemotherapy was carried out in the Hospital of Nagoya University, School of Medicine are shown. The rituximab-containing chemotherapies were performed in 124 cases in about 5 years from the end of 2001 to 2006, and in 36 cases (29%) among 124 cases, recurrence or relapse were observed. In 19 cases, about half of these cases, tissue biopsies were carried out again, and in 5 cases (26.3% among the cases subjected to rebiopsy), negative conversion of CD20 expression was confirmed. Prognoses of the cases where CD20 was negatively converted were extremely bad, and patients in all the cases died within 1 year after the confirmation of negative conversion.

BEST MODE FOR CARRYING OUT THE INVENTION

Description of Terms

For the sake of simplicity, definitions and meanings of a part of terms used in the present specification will be described in summary.

"CD20 (clusters of differentiation 20) (or CD20 antigen)" is a phosphorylated protein having a molecular weight of 33 to 37 kDa, and is considered to be associated with activation and proliferation of B cells. CD20 is one of B-cell surface markers and its expression is observed in a most part of B-cell malignant lymphoma and chronic lymphatic leukemia cells in addition to mature B cells.

"CD20 positive B-cell malignant lymphoma" indicates B-cell malignant lymphoma in which CD20 expression is observed, and includes follicular B-cell non-hodgkin lymphoma, diffuse large B-cell malignant lymphoma, mantle cell lymphoma, and the like.

"CD20 negatively converted B-cell malignant lymphoma" indicates a pathological condition in which original CD20 positive B-cell malignant lymphoma is led to evaluation of being CD20 negative by generating significant decrease of the CD20 protein expression level. Such conversion from CD20 positive to CD20 negative is expressed by "CD20 negative conversion" in the present specification. Occurrence of CD20 negative conversion has been experienced by continuous use of a CD20-directed molecular targeting drug (for example, rituximab).

The "CD20-directed molecular targeting drug" is a compound designed for targeting CD20, and indicates a drug exerting effects via an action to CD20. Currently, as CD20-directed molecular targeting drugs, rituximab, ibritumomab ($^{90}$Y Ibritumomab), and tositumomab ($^{131}$I Tositumomab) are practically used for cancer treatment. Rituximab is provided by the name of Rituxan (registered trademark, Biogen Idec Ltd.), ibritumomab is provided by the name of Zevalin (registered trademark, Biogen Idec Ltd.), and tositumomab is provided by the name of BEXXAR (registered trademark, Glaxo SmithKline K.K.).

(CD20 Negatively Converted B-Cell Malignant Lymphoma Cell Line)

The first aspect of the present invention relates to a CD20 negatively converted B-cell malignant lymphoma cell line (hereinafter referred to as "cell line of the present invention"). The cell line of the present invention is derived from B-cell malignant lymphoma in which CD20 protein expression is negatively converted. That is, the cell line of the present invention is established from B-cell malignant lymphoma cells in which original CD20 positive B-cell malignant lymphoma is led to evaluation to be CD20 negative. For example, the cell line of the present invention can be established by isolation of mononuclear cells from the peripheral blood of a patient having CD20 negatively converted B-cell malignant lymphoma and subsequent culture. As shown in Examples described later, the present inventors have succeeded in establishing a CD20 negatively converted B-cell malignant lymphoma cell line from a patient who was first diagnosed to have follicular lymphoma, which was transformed and recurred to CD20 negative diffuse B-cell malignant lymphoma after treatment with rituximab. The cell line (RRBL1) was deposited to the designated depository institution as follows and is easily available.

Depositary institution: National institute of Advanced Industrial Science and Technology (independent administrative institution), International Patent Organism Depositary (Zip code: 305-8566, Chuo 6, 1-1-1 Higashi, Tsukuba, Ibaraki, Japan)

Deposition date: Sep. 20, 2006

Accession no.: FERM P-21026

Note that the above cell line (RRBL1) is transferred to the international deposit as follows based on the relegation request dated on Sep. 12, 2007.

International depository institution: National institute of Advanced Industrial Science and Technology (independent administrative institution), International Patent Organism Depositary (Zip code: 305-8566, Chuo 6, 1-1-1 Higashi, Tsukuba, Ibaraki, Japan)

Acceptance No.: FERM ABP-10910

Accession No.: FERM BP-10910

As a result of studies by the present inventors, it was revealed that significant decrease of the CD20 mRNA expression was generated. That is, it was found that CD20 protein expression level was negatively converted due to the decrease of the CD20 mRNA expression level. Thus, one of mechanisms of acquiring resistance to a molecular targeting drug was revealed by establishment of RRBL1.

It was also revealed that RBBL1 retains CD20 protein expression ability, in other words, has potential ability to express CD20 protein.

Herein, considering greatness of specificity and universality of action mechanisms of a molecular targeting drug, in a cell line established from pathological conditions acquiring resistance to a CD20-directed molecular targeting drug, CD20 protein expression is negatively converted due to decrease in CD20 mRNA expression level in the same manner as RRBL1, and probability of having 1 potential ability to express CD20 is high. That is, a cell line in which CD20 negative conversion occurs by decrease in an mRNA expression level reversibly can be possibly established from various pathological conditions acquiring resistance to a CD20-directed molecular targeting drug in the same manner as RRBL1.

According to further studies by the present inventors, it was found that RRBL1 is CD10 positive, CD19 positive, CD20 negative, and immunoglobulin light chain (κ chain and λ chain negative (B-cell markers), CD2 negative, CD3 negative, CD4 negative, CD5 negative, CD7 negative, CD8 negative, CD56 negative (T cell or NK cell markers), CD11c negative, CD16 negative, CD25 positive, CD30 negative and CD34 negative (see FIG. 12).

(Model Animal)

The second aspect of the present invention relates to a model animal prepared by using the cell line of the present invention. The model animal of the present invention is prepared by transplanting or administering the cell line of the present invention to an immunodeficient non-human animal, and reflects characteristic pathological conditions corresponding to a cell line to be used. By this feature, the model animal is useful as an in vivo model for studying a therapeutic strategy against pathological conditions corresponding to the used cell line. For example, by using the model animal of the present invention, it is possible to examine effects and side effects of candidate therapeutic drugs, to examine change of a CD20 expression level in the tissue level, and the like.

Although pathological conditions reflected in the model animal of the present invention differ depending on a cell line to be used, typically infiltration of tumor cells into the liver, spleen, kidney, bone marrow, and the like is observed in the model animal of the present invention as pathological findings.

Further, as shown in Examples described later, the present inventors have succeeded in preparation of a model mouse preferably reflecting pathological conditions of a patient, the source of RRBL1.

Herein, a method for transplanting or administering cells to an immunodeficient non-human animal may be followed by a general method, and subcutaneous injection, intraperitoneal injection, transvenous injection, etc can be adopted (see a technical document such as Genetic Engineering, additional volume, Mouse Anatomy Illustrated (written by Shintaro Nomura, Shujunsha)). Kinds of the immunodeficient non-human animals to be used are not particularly limited, BALB/c nude mice, BALB/cA nude mice, NU/NU mice, NIH-III nude mice, Fox Chase Scid mice, Fox Chase Scid Beige mice, Fox Chase Scid Ourbred mice, NOD/SCID mice, NOG mice, nude rats, and the like may be used. Among these, NOD/SCID mice and NOG mice are particularly preferable from the viewpoint of implantation property. Note that the above various immunodeficient non-human animals are available from CLEA Japan, Inc. (Tokyo, Japan), Charles River Laboratories Japan, Inc. (Yokohama, Japan), Charles River Laboratories (Wilmington, Mass., USA), Taconic (New York, USA), and the like.

(Screening Method)

The third aspect of the present invention relates to a method for screening a substance which is efficacious against CD20 positive B-cell malignant lymphoma or CD20 negatively converted B-cell malignant lymphoma. In the first embodiment of the screening method of the present invention, (1) a step of culturing CD20 negatively converted B-cell malignant lymphoma cells in the presence of a test substance, and (2) a step of measuring a CD20 mRNA expression level or a CD20 protein expression level in the cells after culturing to evaluate CD20 expression inducing ability of the test substance are performed.

A substance selected in the screening method of the present invention (screening resultant) is a promising candidate (lead compound) as an active ingredient of a drug against CD20 positive B-cell malignant lymphoma or CD20 negatively converted B-cell malignant lymphoma under the condition of being used together with a CD20-directed molecular targeting drug (hereinafter, a "molecular targeting drug" indicates a "CD20-directed molecular targeting drug" unless otherwise stated). When the selected substance has sufficient effects, it can be directly used as the active ingredient of the drug. On the other hand, even when the selected substance does not have sufficient effects, alteration such as a chemical modification is carried out to increase its drug effects and then the substance can be provided in use as the active ingredient of the drug. Certainly, also when the selected substance has sufficient effects, the same alteration can be carried out for the purpose of increasing further effects.

The screening resultant has CD20 expression inducing ability. When the screening resultant is applied to CD20 positive B-cell malignant lymphoma, it inhibits CD20 positive B-cell malignant lymphoma cells from acquiring resistance to a molecular targeting drug by this CD20 expression inducing ability, and even if CD20 is positive, by promoting further CD20 expression against B-cells whose expression level is not comparatively high, an environment where the molecular targeting drug preferably acts is produced. On the other hand, when the screening resultant is applied to CD20 negatively converted B-cell malignant lymphoma, CD20 negatively converted B-cell malignant lymphoma cells are converted to be sensitive to the molecular targeting drug and an environment where the molecular targeting drug exerts effects again is produced. As described above, the screening resultant is expected to bring effective therapeutic outcomes against both CD20 positive B-cell malignant lymphoma and CD20 negatively converted B-cell malignant lymphoma.

Hereinafter, the screening method of the present invention will be more specifically described by each step.

(1) Culturing Step

In this step, CD20 negatively converted B-cell malignant lymphoma cells are prepared and are subjected to culturing in the presence of a test substance. It is a matter of course to be able to use the cell line (for example, RRBL1) of the present invention described above as the CD20 negatively converted B-cell malignant lymphoma cells, but cells that are not formed into a cell line can also be used. That is, cells obtained from a patient having CD20 negatively converted B-cell malignant lymphoma may be directly subjected to the screening method of the present invention. Note that "directly" used herein means that an operation for forming a cell line is not performed, and the word does not intend to restrict operations generally required for application in the screening method, such as separation and washing.

The number of cells to be used is not particularly limited and can be determined by considering detection sensitivity, experimental facility, and the like. For example, $1\times10^2$ to $1\times10^6$ of cells can be used in one screening operation.

An existential amount (adding amount) of a test substance in a culture medium can be arbitrarily set, and it is preferable to set the adding amount within the range not giving a fatal effect when normal cells are cultured in the same conditions. A person skilled in the art can set an appropriate adding amount by a preliminary experiment.

A culturing time is set so as to sufficiently evaluate the action and effect of the test substance, but is not particularly limited. For example, the culturing time can be set within the range of 1 minute to 10 days. In addition, when a substance showing the desired action and effect is found, a culturing time in screening thereafter can be set based on a time required until the substance indicates the action and effect. For example, since it was revealed that in an experiment using RRBL1 as described in Examples below, 5-aza-2'-deoxycytidine induces CD20 expression by culturing for about 1 to 7 days, the culturing time can be set within the range of 1 to 7 days based on this finding as long as in the screening method using RRBL1.

As a test substance subjected to the screening method of the present invention, organic compounds having various molecular weights (nucleic acid, peptide, protein, lipid (simple lipid, complex lipid (such as phosphoglycede, sphingolipid, glycosylglyceride, and cerebroside), prostaglandin, isoprenoid, terpen, steroid, vitamin, hormone, etc.)) or inorganic compounds can be used. The test substance may be derived from natural products, or may be synthesized. In a case of the latter, for example by use of a procedure of combinatorial synthesis, an efficient screening system can be constructed. Note that a cell extract solution, a culture supernatant, etc may be used as a test substance.

Herein, as described above, it was revealed that CD20 negative conversion occurs due to decrease in the CD20 mRNA expression level by studies using RRBL1. According to this finding, it is preferable to use compounds that improve a transcription rate by giving an effect on transcriptional regulation of CD20 genes (DNA methylase inhibitor, histone deacetylase inhibitor, histone methylase inhibitor, RNA interference (siRNA), nucleic acid and protein aptamer, small peptide, dominant negative protein, etc.) as a test substance.

(2) Measurement and Evaluation Step

In this step, a CD20 mRNA expression level or a CD20 protein expression level (hereinafter, these two levels are collectively referred to as a "CD20 expression level") in cells after culturing are measured and CD20 expression inducing ability of a test substance is evaluated. For measurement of the CD20 mRNA expression level, general methods such as a PT-PCR method (including the real time method), and various hybridization methods using specific probes (for example, northern hybridization and in situ hybridization) can be adopted. The CD20 protein expression level can be measured by using a compound specifically binding to CD20 protein. Measurement of the CD20 protein expression level is preferably performed by an immunological technique, although not limited thereto. An antibody against specific protein is used in an immunological technique, and the protein is detected by bonding property (bonding amount) of the antibody as an index. The term "antibody" used herein includes a polyclonal antibody, a monoclonal antibody, a chimeric antibody, a single strand antibody, a CDR graft antibody, a humanized antibody, or fragments thereof, etc. An antibody in the present invention can be prepared by use of an immunological technique, a phage display method, a ribosome display method, or the like.

An immunological detection method enables prompt and sensitive detection. In addition, an operation is also simple and easy. Note that examples of a detection method include methods such as an ELISA method, radio immunoassay, flow cytometry (FCM), immunoprecipitation, immunostaining, and immunoblotting.

Using a labeled antigen makes it possible to easily perform the above-described measurement. For labeling an antibody, for examples, fluorescent pigments such as fluorescein, rhodamine, Texas red and Oregon green, enzymes such as horseradish peroxidase, microperoxidase, alkaline phosphatase, and β-D-galactosidase, chemical or biological luminescent compounds such as luminol and acridine dye, radioactive isomers such as $^{32}P$, $^{131}I$ and $^{125}I$, and biotin can be used.

CD20 expression inducing ability of a test substance is evaluated by using the measurement results. For example, cells cultured in the presence of the test substance (test group) and cells cultured in the absence of the test substance (control group) are prepared, and CD20 expression levels are measured in respective groups and compared each other. From the compared results, a degree of change in CD20 expression levels (expression level change) is found as a result of existence of the test substance. When the CD20 expression level of the test group is large as compared with the control group, that it, when CD20 expression inducing ability is observed in the test substance, it can be determined that the test substance is efficacious against CD20 positive B-cell malignant lymphoma or CD20 negatively converted B-cell malignant lymphoma. When significant increase of the CD20 expression level was observed in the test group, it can be determined that efficiency of the test substance is particularly high.

In addition, when a CD20 expression level in the absence of the test substance is previously found, this expression level can also be used as an expression level of the control group. Further, also by comparing CD20 expression levels before and after culturing in the presence of the test substance, CD20 expression inducing ability of the test substance can be evaluated.

In one embodiment of the present invention, measurement of the CD20 expression level is performed over time and a plurality of measurement results at different measurement time points are to be obtained, and by using the obtained plurality of measurement results, CD20 expression inducing ability of the test substance is evaluated. When the evaluation was based on such measurement with time, lots of useful information can be obtained for evaluating efficacy of the test substance such as an action mechanism and a maintenance time of the test substance.

After the above steps (1) and (2), the following steps (3) to (5) may be carried out:

(3) a step of culturing CD20 negatively converted B-cell malignant lymphoma cells in the presence of a test substance selected based on the result of the step (2);

(4) a step of culturing the cells after the step (3) in the presence of a CD20-directed molecular targeting drug; and (5) a step of measuring the number of survival cells to determine efficacy of the test substance.

By performing these steps, it can be confirmed whether if the test substance selected in the steps (1) and (2) actually shows therapeutic effects or not when used with a molecular targeting drug. Details of each step will be described hereinafter, however as for matters not particularly mentioned here, descriptions corresponding to the steps (1) and (2) may be used.

(3) Culturing Step (in the Presence of Selected Test Substance)

In this culturing step, CD20 negatively converted B-cell malignant lymphoma cells are cultured under the presence of a test substance recognized to have CD20 expression inducing ability. CD20 negatively converted B-cell malignant lymphoma cells used herein may be the same or different kind of the cells used in the step (1). An example for the latter include a case of using CD20 negatively converted B-cell malignant lymphoma obtained from a patient who is different from the patient from which the cells used in the step (1) are derived. RRBL1 can also be used as CD20 negatively converted B-cell malignant lymphoma cells.

(4) Culturing Step (in the Presence of Molecular Targeting Drug)

This culturing step is carried out in the presence of a molecular targeting drug. As the molecular targeting drug, rituximab, ibritumomab, or tositumomab can be preferably used, but the drug is not limited thereto.

An existential amount (adding amount) of a molecular targeting drug in a culture medium can be arbitrarily set, and it is preferable to set the adding amount within the range not giving a fatal effect when normal cells are cultured in the same conditions. A person skilled in the art can set an appropriate adding amount by a preliminary experiment.

A culturing time is set at a sufficient time for exerting actions of a molecular targeting drug. For example, the culturing time herein can be set within the range of 1 minute to 10 days.

(5) Measurement and Evaluation Step

In this step, the number of survival cells after culturing is measured and the cell killing effect by actions of the test substance and the molecular targeting agent is evaluated. Efficacy of the test substance is determined based on the evaluation results. For example, a group in which the steps (3) and (4) are preformed (test group) and a group in which the step (4) is only performed (that is, a group in which only culturing in the presence of the molecular targeting drug is carried out: control group) are prepared, and the number of living cells after culturing are measured in each group and compared each other. From the compared results, a degree of change in a cell survival rate is found as a result of performing culture in the presence of the test substance. When the number of living cells in the test group is small (cell survival rate is law) in comparison to the control group, that is, when the ability to enhance an action and effect of the molecular targeting drug is recognized in the test substance, the test substance can be determined to be efficacious. When significant decrease in the cell survival rate was observed in the test group, efficacy of the test substance can be determined to be particularly high.

Also by comparing the cell numbers before and after culturing in the test substance, not by setting the control group, efficacy of the test substance can be determined. However, setting such a control group as described above can obtain a result with higher reliability.

In addition, the measurement in this step is performed over time and determination may be made based on a plurality of measurement results.

In one embodiment of the present invention, the following steps (3) and (4) are carried out in place of the above steps (3) to (5):

(3) a step of culturing CD20 positive B-cell malignant lymphoma cells and CD20 negatively converted B-cell malignant lymphoma cells in the presence of the test substance selected based on a result of the step (2) and a CD20-directed molecular targeting drug; and (4) a step of measuring the number of survival cells to determine efficacy of the test substance.

By performing these steps, it can be examined whether if the test substance selected in the steps (1) and (2) actually indicates therapeutic effects or not when administered at the same time with a CD20-directed molecular targeting drug used with a molecular targeting substance. When CD20 positive B-cell malignant lymphoma cells are adopted as cells subjected to the culturing step, the therapeutic effects on CD20 positive B-cell malignant lymphoma can be studied. On the other hand, when CD20 negatively converted B-cell malignant lymphoma cells are adopted, therapeutic effects on CD20 negatively converted B-cell malignant lymphoma can be studied.

Culturing is performed under the condition of coexisting a test substance and a molecular targeting drug in this embodiment. In a measurement and evaluation step carried out subsequently after the culturing step, the number of survival cells after culturing is measured and the cell killing effect by actions of the test substance and the molecular targeting drug is evaluated in the same manner as in above step (5). Efficacy of the test substance is then determined based on the evaluation results. As control groups, cells cultured in the absence of the test substance and in the presence of the molecular targeting drug and cells cultured in the absence of the test substance and the molecular targeting drug can be used.

Note that as for matters not particularly mentioned here, corresponding descriptions as stated above may be used.

The present invention further provides a method of screening a substance giving preferable therapeutic effects when used in combination with a CD20-directed molecular targeting drug. In the screening method herein, the cell line of the present invention (RRBL1, etc) is used. Specifically, the following two types of screening methods are provided.

The First Embodiment

A method for screening a substance which is efficacious against CD20 positive B-cell malignant lymphoma or CD20 negatively converted B-cell malignant lymphoma, including the steps of:
(1) culturing the cell line of the present invention in the presence of a test substance;
(2) culturing the cells after the step (1) in the presence of a CD20-directed molecular targeting drug; and
(3) measuring the number of survival cells to determine efficacy of the test substance.

The Second Embodiment

A method for screening a substance which is efficacious against CD20 positive B-cell malignant lymphoma or CD20 negatively converted B-cell malignant lymphoma, including the steps of:
(1) culturing the cell line of the present invention in the presence of a test substance and a CD20-directed molecular targeting drug; and
(2) measuring the number of survival cells to determine efficacy of the test substance.

The present invention further provides a screening method using the model animal of the present invention. According to the screening method, a substance effective against CD20 negatively converted malignant lymphoma can be selected by an experiment in an in vivo level. Specifically, the following screening method is provided:

a method for screening a substance which is efficacious against CD20 negatively converted B-cell malignant lymphoma, including the steps of:
(1) administering a test substance to the model animal of the present invention; and
(2) examining change of pathological conditions characteristic to CD20 negatively converted B-cell malignant lymphoma indicated in the model animal.

Details of each step will be described hereinafter, however as for matters not particularly mentioned, corresponding descriptions as stated above may be used.

In the step (1), a test substance is administered to the model animal of the present invention. An administration route is not particularly limited, and a suitable route can be selected from oral administration, intravenous administration (injection), intradermal administration (injection), subcutaneous administration (injection), transdermal administration, intraoral administration, direct administration (injection) to target organs (internal organs), and the like. Note that the "target organs (internal organs)" used herein are organs (internal organs) indicating features of CD20 negatively converted B-cell malignant lymphoma in the model animal, and correspond to, for example, the liver, spleen, kidney, and bone marrow, in which infiltration of tumor cells is observed.

A dosage can be arbitrarily set. For example, it can be set at a maximum dosage as much as possible within the range of not giving a fatal effect on the model animal.

The number of administration can be arbitrarily set. For example, the number of administration is set within the range from 1 to 20 times.

In the step (2), a change of pathological conditions characteristic to CD20 negatively converted B-cell malignant lymphoma is examined by using the model animal after administering the test substance. When improvement of the pathological conditions is observed, the test substance can be determined to be efficacious. The change of the pathological conditions can be examined by, for example, visual observation, immunostaining, histopathological observation, tumor weight measurement, measurement of pleural fluid and ascites fluid, protein extraction, RNA extraction, FCM, and the like of the target organs (internal organs). Preferably, a model animal to which the test substance is not administered is prepared (control group) and pathological conditions are compared between the test group and the control group to determine efficacy of the test substance.

(Drug)

A further aspect of the present invention provides a drug against CD20 positive B-cell malignant lymphoma or CD20 negatively converted B-cell malignant lymphoma, which is characterized by containing a compound for increasing a CD20 protein expression level, based on the findings obtained by the study using RRBL1, that is, the findings in which one factor of CD20 negative conversion is the epigenetic change of CD20 mRNA and reexpression of CD20 protein is possible in CD20 negatively converted B-cell malignant lymphoma cells. The drug of the present invention is used together with a molecular targeting drug. However, the drug of the present invention can be constituted as a mixed preparation with a molecular targeting drug (described later), and in such a case, the mixed preparation can be used alone.

When the drug of the present invention is used against CD20 positive B-cell malignant lymphoma, the drug prevents CD20 positive B-cell malignant lymphoma cells from acquiring resistance to a molecular targeting drug by repressing or inhibiting decrease in a CD20 expression level. Accordingly, an environment allowing the molecular targeting drug to continuously act is created, thereby giving preferable therapeutic effects. Further, also in B-cells determined to be CD20 positive, when the CD20 expression level is comparatively low, further increasing the expression level can provide an environment allowing the molecular targeting drug to more effectively act. On the other hand, when the drug is used against CD20 negatively converted B-cell malignant lymphoma, the drug of the present invention promotes reexpression of CD20 protein, thereby transforming the CD20 negatively converted B-cell malignant lymphoma cells to a phenotype indicating sensitivity to the molecular targeting drug. As a result, a molecular targeting drug can act again, which causes preferable therapeutic effects.

The "compound increasing a CD20 protein expression level" used herein may increase a CD20 protein expression level by acting in any of steps of transcription, translation or modification after translation of CD20 genes.

As a result of the study using RRBL1, it was revealed that negative conversion of CD20 and a change in a CD20 mRNA expression level are closely related with each other. As this fact is considered, increasing the CD20 mRNA expression level can be effective as a means for increasing a CD20 protein expression level. Thus, as the "compound increasing a CD20 protein expression level" in the present invention, compounds improving a transcription rate by giving an effect on transcriptional regulation of CD20 genes (for example, DNA methylase inhibitor, histone deacetylase inhibitor, histone methylase inhibitor, RNA interference (siRNA), nucleic acid and protein aptamer, small peptide, dominant negative protein, etc.) are preferably used. As shown in Examples described below, when a DNA methylase inhibitor or a histone deacetylase inhibitor is used against CD20 negatively converted B-cell malignant lymphoma cells, it was confirmed that a CD20 mRNA expression level was increased. Thus, in one preferable embodiment of the present invention, a DNA methylase inhibitor and/or a histone deacetylase inhibitor is used as an active ingredient.

As the DNA methylase inhibitors, various compounds such as 5-aza-2'-deoxycytidine, 5-azacytidine, 5-fuluoro-2'-deoxycytidine, 5,6-dihydro-5-azacytidine, zebularine, and hydralazine are known, and all of these compounds are prospective candidates of an active ingredient of the drug of the present invention. In the same manner, as the histone deacetylase inhibitors, various compounds such as trichostatin A (TSA), valproic acid, phenyl butyrate, SAHA (suberoylanilidie hydroxamic acid), FR901228 (depsipeptide, FK228), MS-27-275, CHAPS, LAQ824, YM753, PDX101, and LBH589 are known, and all of these compounds are prospective candidates of an active ingredient of the drug of the present invention. Various derivatives obtained from known DNA methylase inhibitors or istone deacetylase inhibitors subjected to alteration to a degree of not damaging effects thereof can be used as the DNA methylase inhibitor or histone deacetylase inhibitor in the present invention.

The drug of the present invention may be constituted by combining (using together with) two or more of compounds classified into DNA methylase inhibitors or histone deacetylase inhibitors. Examples thereof include a combination of different kinds of DNA methylase inhibitors, a combination of one kind or two or more kinds of DNA methylase inhibitors and one kind or two or more kinds of histone deacetylase inhibitors and the like, and a combination in this case is arbitral.

In one embodiment of the present invention, the molecular targeting drug is contained in the drug of the present invention. Such a drug can be expected to have the same therapeutic effects as described above by single use thereof.

Preparation of the drug of the present invention can be performed according to the general method. In a case of preparation, other components acceptable for preparation (such as carriers, diluents, disintegrating agents, buffers, emulsifiers, suspending agents, soothing agents, stabilizers, preserving agents, antiseptics, and physical serine water) can be contained. As a diluent, examples such as lactose, starch, sorbitol, D-mannitol, and white sugar can be used. As a disintegrating agent, examples such as starch, carboxymethyl cellulose and calcium carbonate can be used. As a buffer, examples such as a phosphoric salt, a citric salt, and an acetic salt can be used. As an emulsifier, examples such as gum Arabic, sodium alginate, and Tragacanth can be used. As a suspending agent, examples such as glyceryl monostearate, aluminum monostearate, methyl cellulose, carboxymethyl cellulose, hydroxymethyl cellulose, and sodium lauryl sulfate can be used. As a soothing agent, examples such as benzyl alcohol, chlorobutanol, and sorbitol can be used. As a stabilizer, examples such as propylene glycol, diethylin sulfite, and ascorbic acid can be used. As a preserving agent, examples such as phenol, benzalconium chloride, benzyl alcohol, chlorobutanol, and methyl 4-hydroxybenzoate can be used. As an antiseptic, examples such as benzalconium chloride, paraoxybenzoic acid, and chlorobutanol can be used.

A content of the active ingredient in the drug of the present invention differs generally depending on a dosage form, and the content is set at, for example, about 0.001% by weight to about 100% by weight so that a desired dosage can be achieved.

The dosage form of the drug of the present invention is not particularly limited, and the drug of the present invention can be prepared as drops, an injection, a tablet, a spray, a powder, a granule, a capsule, a syrup, an external agent, a suppository, and the like.

(Treatment Method)

The present invention further provides a method for treating CD20 positive B-cell malignant lymphoma or CD20 negatively converted B-cell malignant lymphoma. In the treatment method of the present invention, a DNA methylase inhibitor and/or a histone deacetylase inhibitor, and a molecular targeting drug are used in combination. Preferably, the latter is administered after administration of the former, or the both are administered at the same time. An administration route is not particularly limited, and examples thereof include oral, intravenous, intradermal, subcutaneous, intralymphatic, intramuscular, intraperitoneal, transdermal, and transmucosal administrations. These administration routes are not exclusive each other, and two or more routes arbitrarily selected can also be used together (such as performing intravenous injection simultaneously or after elapse of a predetermined time of oral administration). A "subject" herein is not particularly limited and includes a human and mammals other than a human (including pet animals, livestock animals and experimental animals, specifically, such as mice, rats, guinea pigs, hamsters, monkeys, cattle, pigs, goats, sheep, dogs, cats, chickens and quails). Preferably, the subject in the treatment method of the present invention is a human.

A dosage differs according to the symptoms, age, sex and body weight of a subject to be administered, and a person skilled in the art can appropriately set a suitable dosage based on results of a preliminary experiment (such as an experiment using cells or model animals) and results of a clinical experiment. As an administration schedule, for example, administration of once to several times in one day, once in two days, once in three days, once in four days, once in a week, once in two weeks can be adopted. In setting the administration schedule, pathological conditions of the subject to be administered, a maintenance time of drug effects, and the like can be considered.

Note that as for matters not particularly mentioned herein (such as conditions and operation methods), general methods may be used and can refer to, for example, Molecular Cloning (Third Edition, Cold Spring Harbor Laboratory Press, New York), Current protocols in molecular biology (edited by Frederick M. Ausubel et al., 1987), Current protocols in Immunology, John Wiley & Sons Inc, and the like.

EXAMPLES

Figure 1:
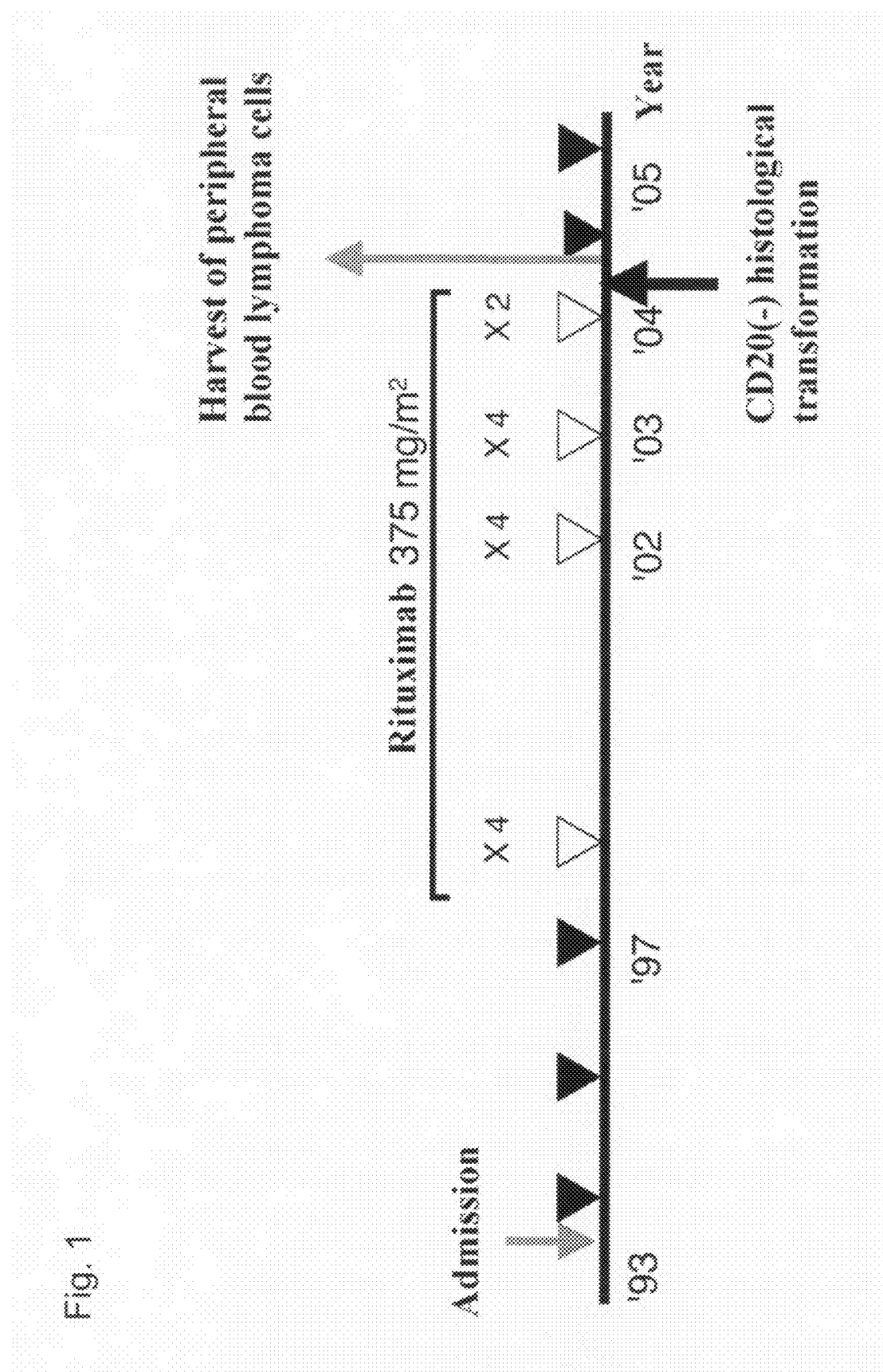
FIG. 1 is a clinical course of a patient, the source of the RRBL1 cell line. The patient was first admitted in 1993. Conventional chemotherapy (black triangles) was carried out by diagnosis of FSC. Further, the chemotherapy in combination with rituximab (white triangles) was performed repeatedly from 1998. The patient's pathological conditions were not in remission, and the chemotherapy was repeatedly carried out when the disease progressed. In 2004, during the chemotherapy in combination with rituximab, aggressive progression of the malignant lymphoma was observed. At this point, the patient's diagnosis was transformation into CD20 negatively converted DLBCL. From this period, a large number of CD20 negative tumor cells were observed in the peripheral blood. Tumor cells were harvested from the peripheral blood in July 2004, and an RBBL1 cell line was established through long-term culturing. Despite that salvage chemotherapy without rituximab was performed to the patient, an effect was low and the leukemic state of the lymphoma was significantly observed, and the patient died in February 2005.

1. Establishment of CD20 Negatively Converted B-Cell Malignant Lymphoma Cell Line (1) Background of Patient Cells were harvested from a patient who is a Japanese 43-year-old man when first admitted. This patient visited the Hospital of Nagoya University, School of Medicine as an outpatient for mainly complaining bilateral cervical lymph node swelling and night sweating. Node lymph swelling throughout the body and splenomegaly on palpation (about 5 cm below the left costal margin) were admitted when visited the hospital. Blood tests showed 9.9 g/dl of hemoglobin and 76,000 of thrombocyte, and anemia and decrease in thrombocyte. The white blood cell and LDH were within the normal range. A biopsy of the left cervical lymph node was performed, and the diagnosis was follicular lymphoma (follicular small cleaved B-cell lymphoma: FSC) and showed CD10 (+), CD19(+), CD20(+) and Igκ(+) features by a surface antigen analysis (FCM) (FIG. 12). Thus, the cells of this lymphoma were confirmed to be CD20 positive. In addition, a bone marrow infiltration was confirmed by bone marrow aspirate. Conventional chemotherapy was repeated and partial remission (PR) was obtained (FIG. 1). From 1997, chemotherapy combined with rituximab (375 mg/kg) was performed. Then, chemotherapy combined with rituximab was performed when the disease progressed. Although rituximab was administered 14 times in total, in June 2004, during chemotherapy with rituximab, aggressive tumor growth formed from the lower abdomen to the inguinal area and spleen tumor growth were observed. Infiltration of lymphoma cells that showed CD10(+), CD19(+), Igκ(+) and CD20(−) were confirmed in the bone marrow (FIG. 12). Infiltration of CD20 negative lymphoma cells were confirmed anywhere in the bone marrow. At this point, the patient's diagnosis was transformation to CD20 negative follicular large cell malignant lymphoma (DLBCL). Although salvation chemotherapy without combining with rituximab was then carried out, the disease state progressed, and in July 2004, CD20 negative lymphoma cells were observed also in the peripheral blood and gradually increased in number. Despite chemotherapy, CD20 negative malignant lymphoma cells took pathological conditions of acute leukemia, and the patient died of severe pneumonia in Feb. 20, 2005. After informed concent was obtained from his family, an autopsy was performed. Note that the patient's clinical curse was shown in FIG. 1.

(2) Establishment of RRBL1

After the informed concent, the peripheral blood was harvested from the patient in July 2004. Mononuclear cells were separated by Ficoll-Paque (Amersham Bioscience, Uppsala, Sweden) and subjected to long-term culture in a RPMI1640 culture medium containing 20% fetal calf serum (FSC) (Sigma, St. Louis, Mo., U.S.A.). The cells were passage-cultured for 1 year or more and thus were considered to form a cell line. We named this cell line RRBL1 (Rituximab resistant B-cell lymphoma 1). The chromosomal abnormalities observed in RRBL1 cells and the lymphoma cells obtained from the patient having the original RRBL1 cells were shown in FIG. 2. Reciprocal translocation between the first chromosome and the seventh chromosome of t(1;7)(p36;p15) and reciprocal translocation between the fourteenth chromosome and the eighteenth chromosome of t(14;18) (q32;q21) were conserved in the both cells. In order to confirm a specific break point of t(14;18) (q32:q21), PCR was performed using a primer specific to a junction of BCL2/JH (FIG. 3C). Genomic DNA was prepared from RRBL1 cells sampled in different culturing stages and the patient's malignant lymphoma cells obtained in different clinical stages and used in study by the PCR (FIG. 3D). A single band at about 800 bp was amplified in all samples (FIG. 3D, lanes 1 to 4). These results confirmed that RRBL1 cells are basically derived from the same clone as that obtained from the patient's CD20 negative lymphoma cells.

2. Analysis of RRBL1 and Clarification of Resistance Mechanism (1) Expression of CD20 Antigen in RRBL1

Then, we studied CD20 protein expression in RRBL1 cells. Immunostaining with an anti-CD20 monoclonal antibody was performed with a Cytospin specimen of the RRBL1 cells, but the CD20 protein expression was not detected (FIG. 4A). The CD20 protein expression was confirmed in Burkitt lymphoma cell line Raji used as a positive control (control). Whole-cell lysates were prepared respectively from the Raji cells, RRBL1 cells and NALM6 cells, and western blotting with an anti-CD20 antigen was performed. The NALM6 cells were reported as a CD20 negative cell line and thus used as a negative control (control). As indicated in FIG. 4B, the CD20 protein expression was detected only in the Raji cells, and the NALM6 cells and the RRBL1 cells indicated negative. However, interestingly, CD20 protein expression was detected also in the RRBL1 cells although it was faint (not shown) because of long-term exposure. From the result, a CD20 expression level is very small in the RRBL1 cells, suggesting that the level cannot be detected by FCR and immunostaining.

Then, a CD20 mRNA expression level in the RRBL1 cells was confirmed by quantitative RT-PCR (FIG. 4C). Here, mRNA prepared from the Raji cells was used as a positive control, and mRNA prepared from 293T cells was used as a negative control. The same analysis was made on RNA of lymphoma cells obtained from CD20 positive B-cell malignant lymphoma patients. The result of the experiment confirmed that the CD20 mRNA expression level in the RRBL1 cells is about 100 times lower than that of Raji cells or a patient subject that is a positive control (FIG. 4C). No amplification was observed in the 293T cells of the negative control. Above results suggested that decrease in the CD20 protein expression level in the RRBL1 cells is due to decrease in the mRNA expression level.

Very interestingly, RRBL1 cells were passage-cultured over a long time and thus a subcell line, RRBL2, was established. In RRBL2 cells, CD20 protein expression was confirmed by western blotting in the same manner as in the Raji cells (FIG. 4D). This can be considered to clearly indicate that the RRBL1 cells sustain CD20 protein expression ability. Further, it strongly suggests that some epigenetic adjustment systems work in decrease in a CD20 mRNA expression level.

On the other hand, RNA prepared from the RRBL1 cells was templated and the CDS full length of CD20 genes was amplified by RT-PCR, and subcloned in a T7Ts-Flag vector. The CD20 protein added with a Flag tag was translated by in vitro translation, then SDS-PAGE was performed and western blotting using an anti-Flag antibody was carried out (FIG. 5). The CD20 protein having a normal size was translated (lane 1). Note that gene sequences of 10 clones were sequenced and no genomic mutation was observed.

(2) Resistance to Rituximab

Rituximab (500 mg/ml) was added to a PRMI1640 culture solution containing 10% FCS and the solution was cultured at 37° C. for 2 days, and the number of living cells was measured. Further, Raji cells were cultured under the same conditions (control group). As shown in FIG. 6, proliferation of the Raji cells was significantly repressed by rituximab, but repression of proliferation was not observed in the RRBL1 cells. Thus, it was confirmed that the RRBL1 cells indicates rituximab resistance in vitro.

(3) Reexpression of CD20 mRNA and CD20 Protein 5-aza-2'-deoxycytidine (SIGMA, hereinafter abbreviated as "Aza") was injected to a culture solution of RRBL1 cells, and the cells were washed after 24 hours. After culturing for further 2 days, RNA and the whole-cell lysate was extracted from the cells, and subjected to analyses by RT-PCR and western blotting. As a result, CD20 mRNA expression increased after the Aza treatment (FIG. 7A, RT, lane 2). In the western blotting analysis, the CD20 protein expression was observed after the Aza treatment (FIG. 7A, IB lane 2).

Subsequently, changes with time regarding CD20 mRNA expression and CD20 protein expression were examined (FIG. 7B) Aza was injected to a culture solution on day 0, and cultured at 37° C. for 24 hours (day 1). Then, the cells were washed and further cultured for 1 to 6 days (day 2 to day 7). RNA and protein were extracted from the cells after culturing, and subjected to analyses by western blotting (using anti-CD20 antibody, anti-IRF4 antibody, anti-PU.1 antibody, anti-DNMT1 antibody, and anti-GAPDH antigen) and RT-PCR. Results are shown in FIG. 7C. It can be confirmed that the CD20 protein expression increased from day 1 after Aza injection (lane 4), but the expression level reached peak on day 3 (lane 6) and then decreased. The CD20 mRNA expression indicated the same tendency as the CD20 protein expression (RT, lanes 3 to 8).

IRF4 and Pu.1 are transcriptional factors that have been reported to bind to a CD20 gene promoter. Their expression was observed before Aza injection and tendency of temporal increase of the expression was recognized (lane 5). DNMT1 (DNA methyltransferase 1) has reported to be decomposed by Aza. As reported, significant decrease in DNMT1 expression was observed on day 1 after Aza injection.

(4) CD20 mRNA Expression and CD20 Protein Expression in Injection Combined with Molecular Targeting Drug Aza and TSA (Trichostatin: histone deacetylase inhibitor) were injected singly or in combination to a culture supernatant of RRBL1 cells. The cells were washed after one day from Aza injection. After further cultured for 2 days, protein was extracted from the cells. In the TSA injected group, protein was extracted from the cells at the point of 24 hours from TSA injection. For the group injected in combination use, Aza was first injected and cultured for 1 day. The cells after washed were cultured for 1 day, then TSA was injected thereto, and further, the cells were dissolved after the elapse of one day to extract protein. Thus obtained each sample was subjected to SDS-PAGE, and western blotting using an anti-CD20 antibody and an anti-GAPDH antibody was then performed. Results of the western blotting are shown in FIG. 8A. Combination use of Aza and TSA more strongly induced the CD20 protein expression (FIG. 8A, lane 6).

RRBL1 was cultured in the presence of Aza or in the presence of Aza and TSA, and then, a cell surface antigen was examined by FCM. Cells expressing CD20 antigen (green area) were observed more when using in combination of Aza and TSA as compared with when using Aza alone (FIG. 8B).

RRBL1 cells (untreated group) and RRBL1 cells treated with Aza and TSA (treated group) were respectively cultured for 2 days in the absence of rituximab (●, ■) or in the presence of rituximab (♦, ▲), and the number of living cells were compared (FIG. 8C). Proliferation of the RRBL1 cells treated with Aza and TSA was significantly inhibited by rituximab (▲). This result indicated that the RBLL2 cells in which CD20 protein expression was induced by being treated with Aza and TSA was sensitive to rituximab.

(5) Analysis of CD20 Transcriptional Regulation in CD20 Gene Promoter

A structure of a CD20 gene promoter is shown in FIG. 9A, and a binding domain of transcription factors Pu.1 and IRF4 is present in the CD20 gene promoter. Further, E-box that has been reported that a transcriptional regulator such as Oct2 is bound is present in the downstream.

Chromatin immunoprecipitation (ChIP assay) was performed in a CD20 gene promoter region in the RRBL1 cells. RRBL1 cells treated with Aza and TSA (treated group) and untreated RRBL1 cells (untreated group) were fixed with formalin, chromatin was then extracted, and ChIP assay was performed using an ant-Pu.1 antibody, an anti-IRF4 antibody, an anti-acetylation H4 (Ac-H4) antibody, an anti-Sin 3 antibody, and an anti-HDAC1 antibody. Bound DNA was detected by PCR using a primer shown in FIG. 9A. As shown in FIG. 9B, Pu.1 and IRF4 were bound to the CD20 promoter regardless of presence or absence of a chemical treatment (lanes 5 and 8). By the chemical treatment, an acetylation rate of histone H4 in the CD20 promoter region was increased (lane 10). Sin 3 and HDAC1 that are constitutional proteins of a transcriptional repressor complex were recruited by the promoter before the chemical treatment (lanes 11 and 13), but dissociated after the treatment.

On the other hand, protein was extracted from the RRBL1 cells treated with chemicals, and western blotting using an anti-CD20 antibody and an anti-GAPDH antibody was performed. It was confirmed that Sin 3 protein expression and HDAC1 protein expression themselves were not largely changed according to presence or absence of chemical treatment (FIG. 9C). Thereby, it was suggested that disappearance of Sin 3 and HDAC1 from the CD20 gene promoter shown in FIG. 9B was due to dissociation of the recruited protein.

3. Transplantation of RBBL1 Immunity to Immunodeficient NOD/SCID Mice

The result of the above analysis confirmed that the RRBL1 cells were useful as a model of rituximab-resistant CD20 negatively converted B-cell malignant lymphoma. It is considered that the cell line would become more useful if a transplantation model of RRBL1 to in vivo could be established. Thus, the RRBL1 cells were injected subcutaneously into the dorsal regions of NOD/SCID mice (Central Institute for Experimental Animals (judicial foundation) (Kawasaki-city, Kanagawa)) and studied whether tumors grew or not. Thirty days after the injection, tumor formation was confirmed with the naked eyes, and tumor growth was able be observed for 53 days (FIG. 10). This phenomenon indicates that the RRBL1 cells can be maintained in an environment of the living bodies of the NOD/SCID mice. Next, RRBL1 cells were intravenously administered and tumor formation was observed. Fifty days after transplantation, organs were removed after anesthetizing the mice and the pathologic tissues were examined (FIG. 11, left column). Tumor cells were significantly infiltrated and grown in tumor organs such as the liver, spleen, kidney, and bone marrow, and when immunostaining was carried out, the tumor cells were confirmed to have features of CD20 negative and CD79a positive B-lymphocyte cells. As a result of comparing with autopsy histological findings of a patient from which the RRBL1 cells were derived (FIG. 11, right column), significant infiltration of CD20 negative and CD79a B-cell malignant lymphoma cells in the liver, spleen, kidney, and bone marrow was observed also in the patient's tissues, which was confirmed to indicate pathological findings very similar to the RRBL1 transplanted mice. These results indicate that a RRBL1 cell NOD/SCID transplanted model reflects very well pathological conditions of a patient having the original RRBL1 cell line, strongly suggesting that the model is extremely useful as an in vivo model for studying a novel therapeutic strategy (combination use of a molecular targeting drug, hormone, vitamin etc, not only conventional chemotherapy) against CD20 negatively converted B-cell malignant lymphoma.

4. Discussion

More than 5 years have passed since rituximab was started being clinically used in combination with conventional chemotherapy (such as CHOP therapy) as a molecular targeting drug against CD20 positive malignant lymphoma (Non-patent Documents 15 and 16). It has been successively reported that a recession rate, a disease-free survival rate or a symptom-free survival rate were significantly prolonged by combination use of rituximab (Non-patent Documents 3 to 8). However, even treatment outcomes of B-cell malignant lymphoma by CHOP therapy or the like were improved by combination use of rituximab, the cure rate is far from perfection. A recent report has been indicated that in a CD20 positive B-cell malignant lymphoma patient treated with rituximab, the disease is recurred and relapsed as rituximab-resistant lymphoma (Non-patent Documents 9 to 12). It is not hard to predict that such a problem about rituximab resistance possibly becomes a serious problem more and more from now for treatment of not only initiated but also recurred B-cell lymphoma patients. From these viewpoints, we think that at least two following points should be urgently studied. The first point is a specific analysis of CD20 negative conversion mechanisms and the second point is overcoming the resistance to rituximab.

In about 5 years from September 2001, CD20 positive malignant lymphoma cases subjected to chemotherapy including rituximab in this facility was 124 cases (FIG. 13), and 36 cases (29.0%) in the 124 cases were recurred or relapsed. Rebiopsy of tumors was performed in 19 cases among the recurred and relapsed cases, but in 5 cases among these cases (26.3% in cases of performing rebiopsy), disappearance or decrease of CD20 expression was observed in surface marker detection (FCM) and immunostaining.

We have succeeded in forming RRBL1 cells that are CD20 negatively converted B-cell malignant lymphoma cells into a cell line from a patient transformed to a diffuse large cell malignant lymphoma (DLBCL) by recurring CD20 positive follicular lymphoma to CD20 negative conversion after administering rituximab. CD20 antigen was undetectable in this cell line by FCM and immunostaining. However, by western blotting, CD20 protein expression was confirmed although it was a trace amount, and interestingly, quantitative RT-PCR detected CD20 mRNA expression in a level of about $1/100$ as compared with that of CD20 positive lymphoma cells. This fact strongly suggested that decrease in the mRNA expression level is one important factor of negative conversion of a CD20 surface antigen expression and is a cause of patient's rituximab resistance. Very interestingly, sufficient CD20 protein expression was confirmed in subcell line RRBL2 obtained by culturing RRBL1 for a long time. From this finding, as a result of CD20 mRNA expression being aberrantly repressed because of some reasons, resistance to rituximab was considered to be produced. The causes of the repression of mRNA expression were considered: (1) genetic mutation in the CD20 promoter region; (2) loss of the CD20 gene; (3) the epigenetic change in CD20 mRNA expression, including aberrant CpG methylation (Non-patent Document 17); and (4) abnormalities of transcription factors and transcriptional regulators that regulate CD20 mRNA expression. The possibilities of (1) and (2) are low when considering the fact that CD20 protein expression was recognized in RRBL2.

Recently, genetic mutations in the CD20-coding sequence have been reported as one of causes in acquiring rituximab resistance (Non-patent Document 10). If the genetic mutation occurs in a specific region, it can be understood that such genetic mutation could be associated with resistance mechanism. According to a recent report, it was reported that rituximab exerts its functions by recognizing the higher-order structure of CD20 protein (Non-patent Document 18). However, in the cases we experienced, it was expected that acquisition of resistance to rituximab was due to the fact that rituximab cannot recognize the CD20 antigen by decreasing in a CD20 protein expression level in cell surfaces. If the problem is decrease in the CD20 mRNA expression level, it can be considered that if the CD20 mRNA expression level can be increased, resistance to rituximab can be overcome. That is, induction of CD20 mRNA expression becomes a prospective strategy aiming for overcoming the resistance to rituximab.

Results of our further study strongly suggested that the epigenetic change of CD20 mRNA expression is the principal factor of rituximab resistance. CD20 mRNA expression was induced and CD20 protein can be reexpressed, indicating that such a treatment makes it possible to enhance sensitivity to rituximab. This outcome supports practical efficacy of the strategy such as inducing CD20 mRNA expression.

We also indicated that RRBL1 cells can be transplanted to NOD/SCID mice. An important point is that an infiltration form of tumor cells in the transplanted mice reproduced very well pathological conditions of a patient from which the RRBL1 cells was derived. Thus, RRBL1 cells could be useful not only for analyzing CD20 negative conversion mechanisms in vitro but also very helpful for developing therapeutic strategies against rituximab-resistant CD20 negative B-cell malignant lymphoma in vivo.

INDUSTRIAL APPLICABILITY

The CD20 negatively concerted B-cell malignant lymphoma cell, the model animal, and the screening method provided by the present invention are useful for developing therapeutic strategies for inhibiting or overcoming of resistance to a CD20-directed molecular drug.

The present invention is not limited to the above descriptions of embodiments and Examples of the present invention. Various modifications are also included in the invention within the range where a person skilled in the art can easily conceive without departing from the scope of claims.

Contents of the treatises, published patent bulletins and patent bulletins specified in the present specification are incorporated by reference in their entirety.

The invention claimed is:

1. A cell line specified by accession No: FERM BP-10910.

2. A model animal indicating pathological conditions of CD20 negatively converted B-cell malignant lymphoma, which is prepared by transplanting or administering the cell line according to claim 1 to an immunodeficient non-human animal, wherein said immunodeficient non-human animal is a NOD/SCID mouse.

3. A method for screening a substance which is efficacious against a CD20 negatively converted B-cell malignant lymphoma, comprising the steps of:
   (1) culturing the cell line of claim 1 in the presence of a test substance; and
   (2) measuring a CD20 mRNA expression level or a CD20 protein expression level in the cells after culturing to evaluate CD20 expression inducing ability of the test substance.

4. The method for screening according to claim 3, further comprising the following steps of:
   (3) culturing the cells after step 2 in the presence of a CD20-directed molecular targeting drug; and
   (4) measuring the number of survival cells to determine efficacy of the test substance.

5. A method for screening a substance which is efficacious against a CD20 negatively converted B-cell malignant lymphoma, comprising the steps of:
   (1) culturing the cell line according to claim 1 in the presence of a test substance;
   (2) culturing the cells after step (1) in the presence of a CD20-directed molecular targeting drug; and
   (3) measuring the number of survival cells to determine efficacy of the test substance.

6. A method for screening a substance which is efficacious against a CD20 negatively converted B-cell malignant lymphoma, comprising the steps of:
   (1) culturing the cell line according to claim 1 in the presence of a test substance and a CD20-directed molecular targeting drug; and

SEQUENCE LISTING

<160> NUMBER OF SEQ ID NOS: 2

<210> SEQ ID NO 1
<211> LENGTH: 37
<212> TYPE: DNA
<213> ORGANISM: Homo sapiens

<400> SEQUENCE: 1
gccagacctc cccgggtccc cctactacta ctactac                                    37

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aagaagtgaa acc                                                              13

(2) measuring the number of survival cells to determine efficacy of the test substance.

7. A method for screening a substance which is efficacious against CD20 negatively converted B-cell malignant lymphoma, comprising the steps of:
 (1) administering a test substance to the model animal according to claim 2; and
 (2) examining change of pathological conditions characteristic to CD20 negative B-cell malignant lymphoma indicated in said model animal.

* * * * *